US006576660B1

(12) United States Patent
Liao et al.

(10) Patent No.: US 6,576,660 B1
(45) Date of Patent: Jun. 10, 2003

(54) METHODS AND COMPOSITIONS FOR REGULATION OF 5-α-REDUCTASE ACTIVITY

(75) Inventors: Shutsung Liao, Chicago, IL (US); Richard A. Hiipakka, Chicago, IL (US)

(73) Assignee: Arch Development Corporation, Chicago, IL (US)

( * ) Notice: Subject to any disclaimer, the term of this patent is extended or adjusted under 35 U.S.C. 154(b) by 0 days.

(21) Appl. No.: 09/530,443

(22) PCT Filed: Oct. 30, 1998

(86) PCT No.: PCT/US98/23041
§ 371 (c)(1),
(2), (4) Date: Apr. 28, 2000

(87) PCT Pub. No.: WO99/22728
PCT Pub. Date: May 14, 1999

Related U.S. Application Data

(60) Provisional application No. 60/063,770, filed on Oct. 31, 1997.

(51) Int. Cl.[7] .................. A61K 31/35; A61K 31/44; A61K 31/12; A61K 31/075

(52) U.S. Cl. .................. 514/456; 514/455; 514/453; 514/457; 514/337; 514/532; 514/544; 514/557; 514/617; 514/646; 514/680; 514/690; 514/622; 514/655; 514/720; 514/729; 514/731; 514/732; 514/678; 514/683; 514/558; 514/681; 514/682; 514/679; 564/170; 564/177; 549/399; 568/325

(58) Field of Search .................. 514/456, 455, 514/457, 453, 337, 532, 544, 557, 558, 617, 646, 680, 681, 690, 622, 683, 682, 678, 679, 655, 720, 729, 731, 732

(56) References Cited

U.S. PATENT DOCUMENTS

| | | |
|---|---|---|
| 5,306,486 A | 4/1994 | McCook et al. |
| 5,422,371 A | 6/1995 | Liao et al. |
| 5,605,929 A | 2/1997 | Liao et al. |
| 5,665,367 A | 9/1997 | Burger et al. |
| 5,665,393 A | 9/1997 | Chen et al. |
| 5,686,082 A | 11/1997 | N'Guyen |
| 5,804,168 A | 9/1998 | Murad |
| 5,804,594 A | 9/1998 | Murad |
| 5,962,517 A | 10/1999 | Murand |
| 6,093,411 A | 7/2000 | Bissett |
| 6,180,662 B1 | 1/2001 | Lansendorfer et al. |
| 6,183,731 B1 | 2/2001 | Carey et al. |
| 6,197,808 B1 | 3/2001 | Cheng et al. |
| 6,231,877 B1 | 5/2001 | Vacher et al. |
| 6,248,341 B1 | 6/2001 | Anderson et al. |
| 6,337,320 B1 | 1/2002 | Hersh et al. |

FOREIGN PATENT DOCUMENTS

| | | |
|---|---|---|
| CN | 1079361 | 12/1993 |
| DE | 19627344 | 1/1998 |
| DE | 29813269 | 11/1998 |
| EP | 0003794 | 9/1979 |
| EP | 0116439 | 8/1984 |
| EP | 0309086 | 3/1989 |
| FR | 2734478 | 11/1996 |
| JP | 57448580 | 7/1982 |
| JP | 62084021 | 4/1987 |
| JP | 1025726 | 1/1989 |
| JP | 2300120 | 12/1990 |
| JP | 5139987 | 6/1993 |
| JP | 5279264 | 10/1993 |
| JP | 6128168 | 5/1994 |
| JP | 9315985 | 12/1997 |
| WO | WO 94/01100 | 1/1994 |
| WO | WO 94/09801 | 5/1994 |
| WO | WO 96/37201 | 11/1996 |
| WO | WO 99/22728 | 5/1999 |
| WO | WO 00/61547 | 10/2000 |
| WO | WO 01/26668 | 4/2001 |
| WO | WO 01/49285 | 7/2001 |
| WO | WO 01/72318 | 10/2001 |
| WO | WO 01/72319 | 10/2001 |
| WO | WO 01/74327 | 10/2001 |

OTHER PUBLICATIONS

Miura, T. et al 'preparation of antiallergen formulations for removal of environmental allergens' CA 122:38824 (1995).*

Wang, Zhi Y., et al., *Interaction of Epicatechins Derived From Green Tea With Rat Hepatic Cytochrome P–450*, The American Society for Pharmacology and Experimental Therapeutics, 16(1):98–103, 1988.

Chemical Abstract 108:160935, 1988.

Asai, et al., "Dietary curcuminoids prevent high–fat diet–induced lipid accumulation in rat liver and epididymal adipose tissue," J. Nutr, 2001, 131(11);2932–5.

Bhattacharyya et al., "Analysis of the steroid binding domain of rat steroid 5 alpha–reductase (isozyme–1) the steroif D–ring binding domain of 5–alpha–reductase," Steroids, 1999; 64: 197–204.

Deplewski, et al., "Preputial sebocyte 5 alpha–reductse isoform specificity," Endocrinology, 1997, 138 (10): 4416–20.

Donadio, James V., "Omega–3 polyunsaturated fatty acids: a potential new treatment of immune reanl disease," Mayo Clin Proc, 1991 May: 1018–1028.

Downing, et al., "Essential fatty acids and acne," J Am Acad Dermatrol, 6; 1986 May: 221–5.

Frost, et al., "Inhibitors of sex hormones: development of experiment modes", Adv. Biol. Skin., 1972 May: 403–420.

Harris, et al., "Identification oand selective inhibition of an isozyme of steroid 5 alpha–reductase in human scalp," Prc. Natl. Acad. Sci. USA, 1992 May: 10787–1079.

(List continued on next page.)

*Primary Examiner*—Amelia Owens
(74) *Attorney, Agent, or Firm*—Mayer, Brown, Rowe, & Maw; Joseph A. Mahoney; Christine M. Rebman

(57) ABSTRACT

Compounds that inhibit 5-alpha-reductase are provided. The compounds are used to treat prostate cancer, breast cancer, obesity, skin disorders and baldness.

18 Claims, 10 Drawing Sheets

OTHER PUBLICATIONS

Hiipakka, et al., "Structure–activity relationships for inhibition of human 5 alpha–reductase by polyphenols," Biochem Pharmacol. 2002 Mar 15;63(6): 1165–76.

Hiipakka, et al., "Expression of 5 alpha–reductase in bacteria as a trp E fusion protein and its use in the production of antibodies for imunocytochemical localization of 5 alpha reductase," J Steroid Biochem Mol Biol. 1993 Jun;45(6): 539–48.

Igarashi, Miki and Miyazawa, Teruo, "The growth inhiitory effect of conjugated linoliec acid on a human hepatoma cell line, HepG2, is induced by achange in fatty acid metabolism, but not the facilitation of lipid peroxidation in the cells," Biochim Biophys Acta. 2001 Feb 26;1530(2–3): 162–71.

Kao, et al., "Modulation of obesity by a green tea catechin," Am J Clin Nutr. 2000 Nov;72(5): 1232–4.

Horrobin, et al., "Essential fatty acids in clinical dermatology," J Am Acad Dermatol. 1989 Jun; 20(6): 1045–53.

Khan, et al., "Arachidonic and cis–unsaturated fatty acids induce selective platelet substrate phosphorylation through activation of cytosolic protein kinase C," FEBS Lett. 1991 Nov 4; 292(1–2):98–102.

Komori, et al., "Anticarcinogenic activity of green tea polyphenols," Jpn J Clin Oncol. 1993 Jun;23(3):186–90.

Liang, et al., "Inhibition of testosterone stimulation of the hamster flank organs by y–linolenic acid a five alpha–reductase inhibitor," SID Abstracts, vol. 102 (No. 4), 647.

Liang, et al., "Species differences in prostatic steroid 5 alpha–reductases of rat, dog, and human," Endocrinology. 1985 Aug;117(2);571–9.

Liang, Techming and Liao, Shutsung, "Inhibition of steroid 5 alpha–reductase by specific aliphatic unsaturated fatty acids," Biochem J. 1992 Jul 15;285 ( Pt 2):557–62.

Liang, et al., "Anti–5 alph–reductase autoantibodies in the serum of patients with prostatic cancer," J Clin Endocrinol Metab. 1990 Dec;71(6):1666–8.

Liang, et al., "Growth suppression of hamster flank organs by topical application of y–linolenic and other fatty acid inhibitors of 5 alpha–reductase," J Invest Dermatol. 1997 Aug;109(2);152–7.

Liao, et al., "Growth inhibition and regression of human prostate and breast tumors in athymic mice by tea epitgallocatechin gallate," Cancer Lett. 1995 Sep 25;96(2):239–43.

Liao, S, "The medicinal action of androgens and green tea epigallocatechin gallate," Hong Kong Med J. 2001 Dec;7(4):369–74.

Liao, et al., "Growth suppression of hamster flank organs by topical application of catechins, alizarin, curcumin, and myristoleic acid," Arch Dermatol Res. 2001 Apr;293(4):200–5.

Shutsung, Liao, "Androgen action: Molecular mechanism and medical application," J Formos Med Assoc. 1994 Sep;93(9): 741–51.

Liao, et al., "Selective inhibition of steroid 5 alpha–reductase isozymes by tea ipicatechin–3–gallate and epicallocatechin–3–gallate," Biochem Biophys Res Commun. 1995 Sep 25:214(3):833–8.

Liao, et al., "Green tea: Biochemical and biological bais for health benefits," Vitam Horm. 2001;62:1–94.

Miyazawa, Teruo, "Absorption, metabolism and antioxidative effects of tea catechin in humans," Biofactors. 2000;13(1–4);55–9.

Nagata, et al., "Association of coffe, green tea, and caffine intakes with serum concentrations of estriadiol and sex hormone–binding globulin in premenopausal japanese women," Nutr Cancer. 1998;30(1):21–4.

Rose, David and Connolly, Jeanne, "Effects of fatty acids and dicosanoid synthesis inhibitors on the growth of two human prostate cancer cell lines," Prostate. 1991;18(3);243–54.

Rizvi, Syed and Zaid, Mohammad, "Modulation of erythrocyte membrane NA/K–Atpase activity by insulin in norman and type 2 diabetic patients. evaluation of the insulin–like role of (–) epicatechin," Medical Science Research. 1998. 26: 245–247.

Serafini, Paulo and Lobo, Rogerio, "Increased 5alpha–reductase activity in idiopathic hirsutism," Fertil Steril. 1985 Jan;43(1): 74–8.

Tang, et al., "Green tea polyphenols and vitamin e inhibit angogenesis by supressing il–8," Free Radic Biol Med. 1999. 27: S149.

Taylor, et al., "Photoaffinity labeling or rat steroid 5alpha–reductase (isozyme–1) by a benzopohenone derivative of a 4–methyl–4–azasteroid," Steroids. 1996 May; 61(5):323–31.

Umekita, et al., "Human prostate tumor growth in athymic mice: inhibition by androgens and stimulation by finasteride," Proc Natl Acad Sci U S A. 1996 Oct 15;93(21):11802–7.

Valcic, et al., "Inhibitory effect of six green tea catechins and caffeine on the growth of four selected human tumor cell lines," Anticancer Drugs. 1996 Jun; 7(4):461–8.

Yang, Chung and Wang, Zhi–Yuan, "Tea and cancer," J Natl Cancer Inst. 1993 Jul 7;85(13):1038–49.

Zhu, et al., "Effects of tea polyphenols and flavonoids on liver microsomal glucuronidation of estradiol and estrone," J Steroid Biochem Mol Biol. 1998 Feb;64(3–4):207–15.

Chantre P., and Lairon D., "Recent findings of green tea extract AR25 (exolise) and its activity for the treatment of obesity," Phytomedicine (jena), 2002 Jan; 9(1);3–8.

Sartippour, et al., "Green tea and its catechins inhibit breast cancer xenografts," Nutrition and Cancer. 2001; 40 (2);149–156.

Proniuk, et al., "Preformulation study of epigallocatechin gallate, a promising antioxidant for topical skin cancer prevention." J Pharm Sci. 2002 Jan; 91; 111–6.

Kao, et al., "Modulation of endocrine systems and food intake by green tea epigallocatechin gallate". Endocrinology, 2000, 141 (3): 980–987.

* cited by examiner

FIGURE 1 - FLAVANOIDS
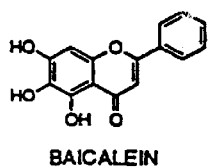
BAICALEIN
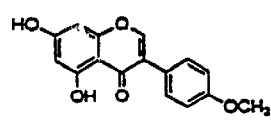
BIOCHANIN A
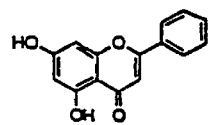
CHRYSIN
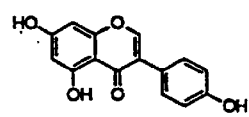
DAIDZEIN
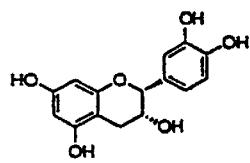
EPICATECHIN
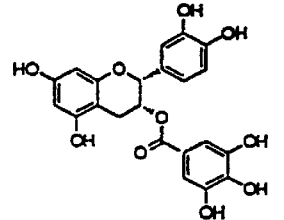
EPICATECHIN GALLATE
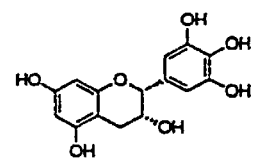
EPIGALLOCATECHIN
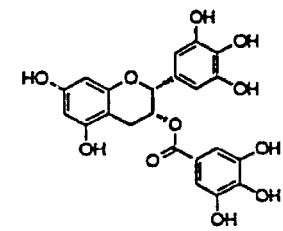
EPIGALLOCATECHIN GALLATE
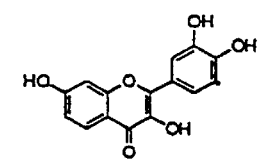
FISETIN
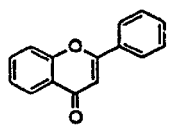
FLAVONE
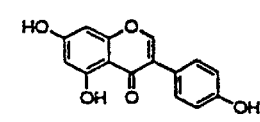
GENISTEIN
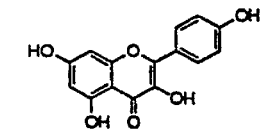
KAEMPFEROL
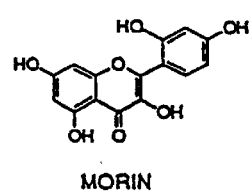
MORIN
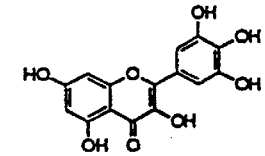
MYRICETIN
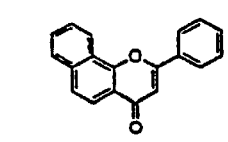
α-NAPTHOFLAVONE
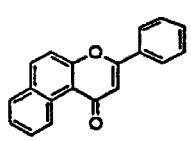
β-NAPTHOFLAVONE
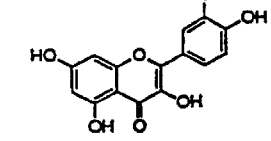
QUERCITIN
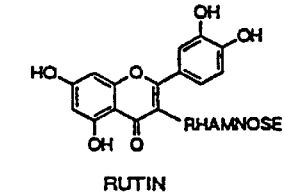
RUTIN
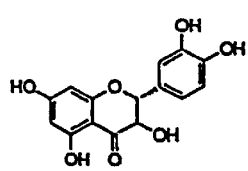
TAXIFOLIN

FIGURE 2 - CATECHOLS
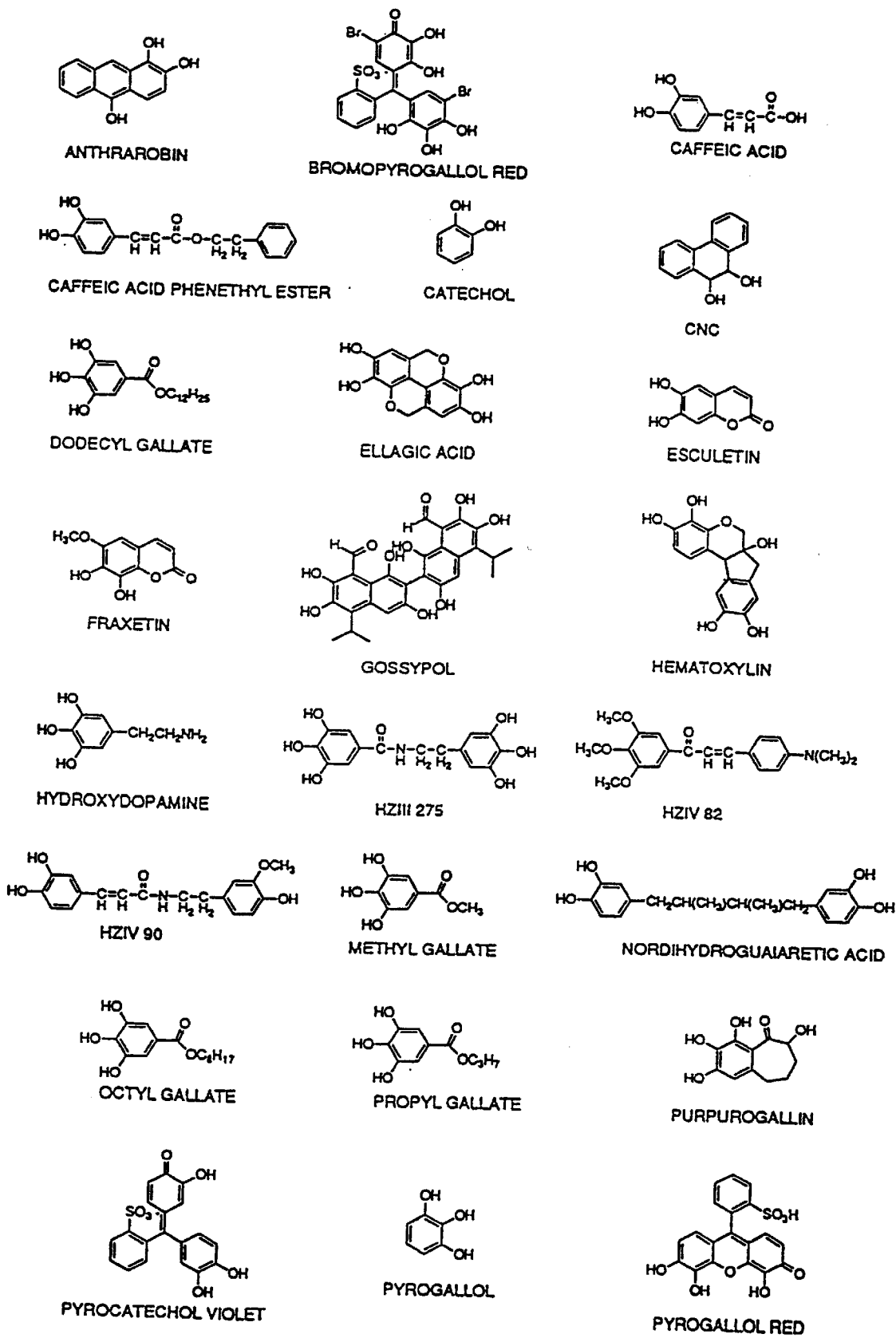

FIGURE 3 - FERULIC ACID DERIVATIVES
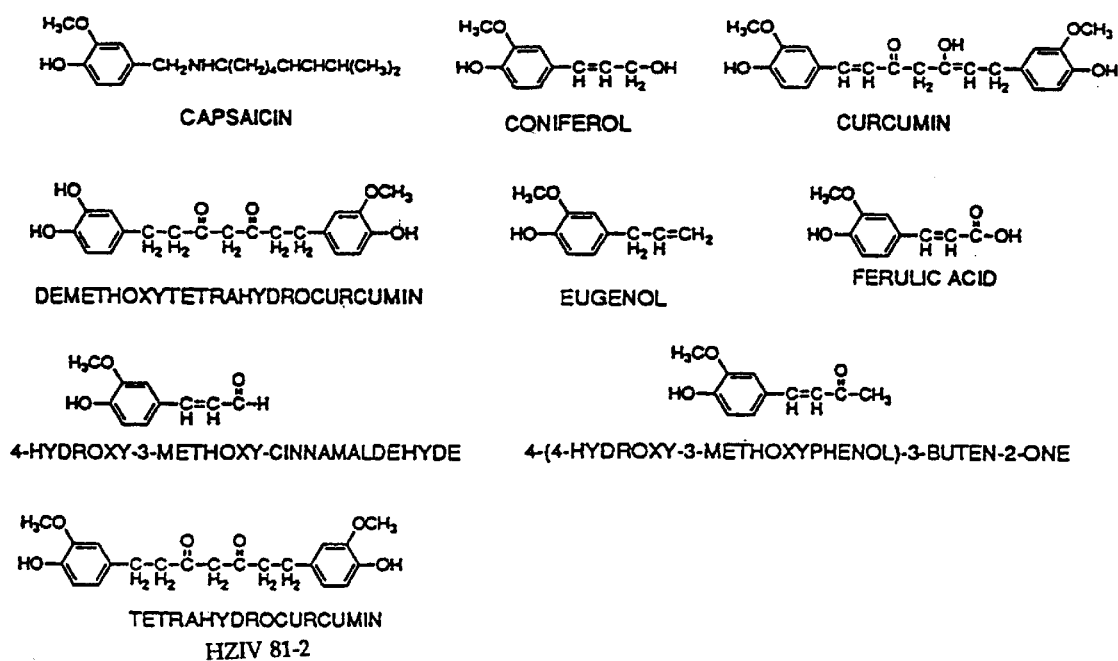

FIGURE 4 - QUINONES
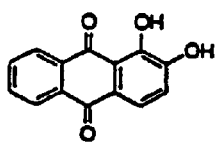
ALIZARIN
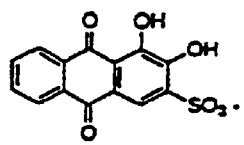
ALIZARIN RED S
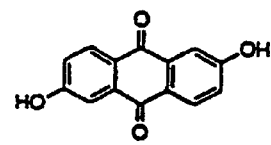
ANTHRAFLAVIC ACID
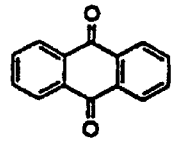
ANTHRAQUINONE
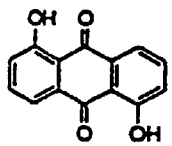
ANTHRARUFIN
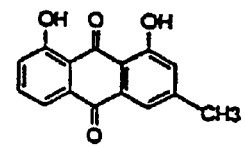
CHRYSOPHANIC ACID
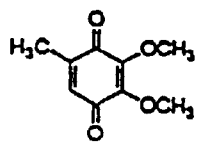
COENZYME Q
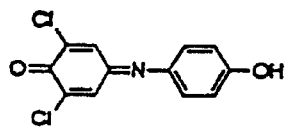
2,6-DICHLOROINDOPHENOL
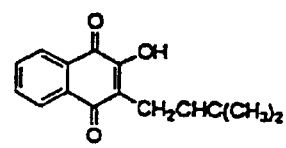
LAPACHOL
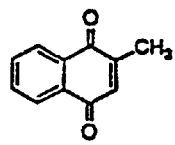
MENADIONE
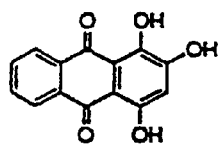
PURPURIN
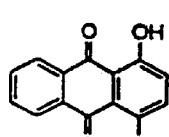
QUINIZARIN
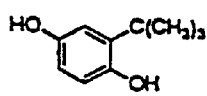
t-BUTYLHYDROQUINONE

FIGURE 5 - EPIGALLOCATECHIN DERIVATIVES
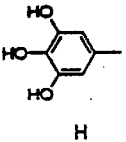
| COMPOUND | R |
|---|---|
| EGCG | 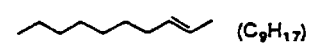 |
| EGC | H |
| HZIV 109 | OH |
| HZIV 145 | $CH_3$ |
| HZIV 169 | $CH_3(CH_2)_4$ |
| HZIV 166 | $CH_3(CH_2)_6$ |
| HZIV 168 |  ($C_9H_{17}$) |
| HZIV 165 | $CH_3(CH_2)_{12}$ |
| HZIV 160 |  ($C_{13}H_{25}$) |
| HZIV 148 | $CH_3(CH_2)_{16}$ |
| HZIV 142 | 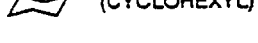 ($C_{17}H_{29}$) |
| HZIV 144 |  (CYCLOHEXYL) |
| HZIV 74 |  |
| HZIV 107 | 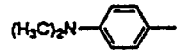 |
| HZIV 92 |  |
| HZIV 120 | 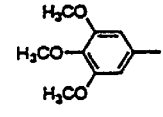 |
| HZIV 63 | 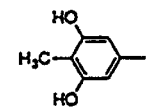 |
| HZIV 68 | 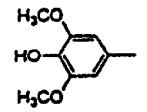 |
| HZIV 75 | 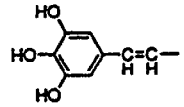 |
| HZIV 134 |  |

FIGURE 6 - EPICALLOCATECHIN DERIVATIVES

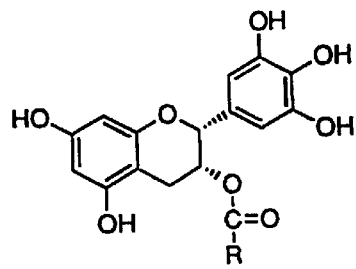

R: a chain with 2 to 20 atoms from the group consisting of carbon, oxygen, sulfur, and nitrogen, without or with one to four double bonds and additional hydrogen. These atoms can be in a straight chain or branched form, or in the form of aromatic ring structures, which may have a substitution of one to three carbon, alkyl, or halogenated alkyl, nitro, amino, methylated amino, carboxyl, or hydroxy groups, or halogen atoms.

FIGURE 7 - GALLATES

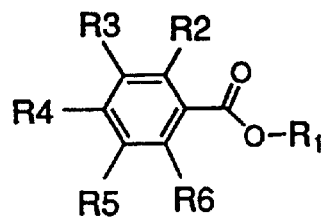

R1: an alkyl chain with 2 to 20 atoms from the group consisting of carbon, oxygen, sulfur, and nitrogen, without or with one to four double bonds and additional hydrogen. These atoms can be in a straight chain or branched form, or in the form of aromatic ring structures, which may have substitution of one to three carbon alkyl or halogenated alkyl, nitro, amino, methylated amino, carboxyl, hydroxy groups or halogen atoms.

R2-5: an alkyl chain with 1 to 12 atoms from the group consisting of carbon, oxygen, sulfur, hydrogen and nitrogen, without or with hydroxy groups. These atoms can be in a straight chain or branched form, which may have substitution of one to three carbon alkyl or halogenated alkyl, nitro, amino, methylated amino, carboxyl groups and hydrogen or halogen atoms.

FIGURE 8 - CURCUMIN DERIVATIVES

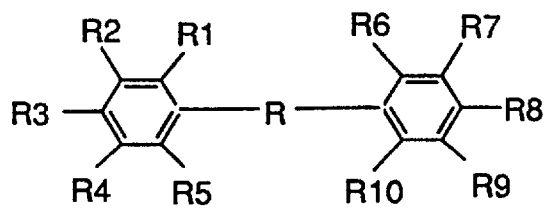

R: An alkyl chain with 1 to 14 atoms from the group consisting of carbon, oxygen, sulfur, and nitrogen, without or with one to three double bonds, carbonyl, or hydroxyl groups and additional hydrogens. These atoms can be in a straight chain or branched form, or in the form of aromatic ring structures which may have substitution of one to three carbon alkyl or halogenated alkyl, nitro, amino, methylated amino, carboxyl, or halogen atoms.

R2-5: Hydroxy or methoxy groups or an alkyl chain with 1 to 10 atoms from the group consisting of carbon, oxygen, sulfur, and nitrogen, without or with hydroxy groups and additional hydrogens. These atoms can be in a straight chain or branched form, which may have substation of one to three carbon alkyl or halogenated alkyl, nitro, amino, methylated amino, carboxyl groups and hydrogen or halogen atoms.

FIGURE 9 - QUINONES AND CATECHOLS
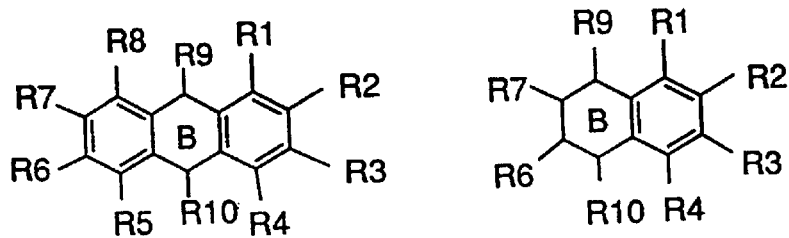
R1 - R8 can be 1 to 6 atoms that may consist of carbon, nitrogen, oxygen, and sulfur, and additional hydrogen or halogen atoms. They can be in the form of alkyl or halogenated alkyl, methoxy, nitro, hydroxy or amino groups. R9 and R10 can be hydroxy groups or in the form of quinones. Ring B can be in a saturated, aromatic or quinine structures.

FIGURE 10 - FATTY ACIDS
CONJUGATED OCTADECADIENIOC ACID: MIXTURE OF CIS AND TRANS 9,11 AND 10,12 OCTADECADIENOIC ACIDS (C18:2)
5,8,11,14-EICOSATETRAYNOIC ACID
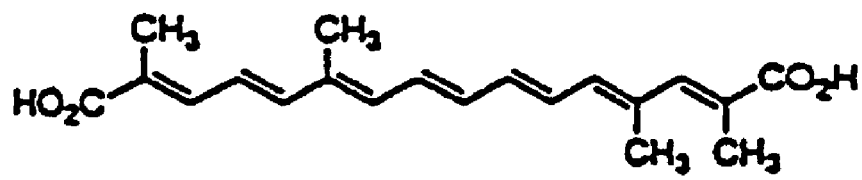
CROCETIN

METHODS AND COMPOSITIONS FOR REGULATION OF 5-α-REDUCTASE ACTIVITY

This application claims benefit of provisional appln No. 60/063,770 Oct. 31, 1997.

TECHNICAL FIELD OF THE INVENTION

The present invention relates generally to compounds, compositions methods regulating the action and function of androgens and other steroid hormones by modulating the activity of steroid-reductases, including isozymes of 5α-reductases. More specifically, the present invention relates to the use of these compounds to regulate processes or treat disorders that are modulated by androgens or other steroid hormones or are caused by abnormal actions of androgens or other steroid hormones in cells or organs of animals, humans, plants, or microorganisms. This invention relates to the use of natural and synthetic flavanoids, catechols, curcumin-related substances, quinones, catechins and fatty acids and their analogues or derivatives as 5α-reductase isozyme inhibitors and as therapeutic agents. These compounds can also be used in promoting or modulating desirable production of specific products for commercial purposes.

BACKGROUND OF THE INVENTION

In some of the androgen-sensitive organs, such as the prostate and skin, testosterone (T) is converted to a more active metabolite 5α-dihydrotestosterone (DHT) by 5α-reductase (Anderson and Liao, 1968; Bruchovsky and Wilson, 1968). Other substrates of 5α-reductases are also converted to reduce products that may have specific properties. Inhibition of 5α-reductase represents a unique approach for developing therapeutic methods for androgen-dependent diseases, such as benign prostatic hyperplasia, breast and prostatic cancer, skin disorders, seborrhea, common baldness, hirsutism, and hidradenitis suppurative. Various compounds have been shown to inhibit 5α-reductase activity (Liang and Liao, 1992; Hirsch et al., 1993; Russell and Wilson, 1994; Liao and Hiipakka, 1995). Finasteride (Proscar), a 5α-reductase inhibitor, lowers the level of DHT in serum and the prostate, reduces prostate volume and increase urinary flow in some patients (Stoner E. Finasteride Study Group, 1992). Certain aliphatic unsaturated fatty acids, such as γ-linolenic acid (Liang and Liao, 1992) and catechin-3-gallates (Liao and Hiipakka, 1995), can inhibit 5α-reductase activity of liver and prostate of rats and humans in vitro.

5α-Reductase is found in many organs (Russell and Wilson, 1994; Hiipakka et al., 1993) including the sebaceous gland of hamsters (Takayasu and Adachi, 1972) and human hair follicles (Randall, 1994). Two 5α-reductase isozymes have been identified in rats and humans (Russell and Wilson, 1994). The type 1 isozyme predominates in rat tissues such as liver, kidney, brain, and lung, whereas the type 2 enzyme is more abundant in rat testis and epididymis. Both isozymes are found in skins of the neonate, but the type 1 isozyme is the major form expressed in the skin after puberty. The type 1 isozyme is also expressed in balding scalp. The possibility that the type 2 isozyme plays a unique role in skin and hair growth cannot be excluded. Finasteride, a 4-azasteroid, is a competitive inhibitor of 5α-reductases and has an affinity 30-fold higher for isozyme 2 than for isozyme 1 (Russell and Wilson, 1994). In contrast, the green tea catechins, epicatechin-3-gallate and epigallocatechin-3-gallate are more effective inhibitors of the type 1 enzyme and γ-linolenic acid inhibits both isozymes equally well (Liao and Hiipakka, 1995).

In the stumptail macaque, a monkey model of androgenic alopecia, finasteride given orally prevents frontal baldness (Diani et al, 1992). The paired hamster flank organs, one on each side of the costovertebral angle, are highly sensitive to androgen stimulation. Topical application of γ-linolenic acid suppresses only the androgen-dependent growth of the treated hamster flank organ without showing systemic effects on the contralateral flank organ and this effect is very likely due to local inhibition of 5α-reductase.

Uses of androgens known to the medical arts include, for example, treatment of hypogonadism and anemia. The abuse of androgens among athletes to enhance performance is well known. Androgens are also known to promote the development of benign prostatic hyperplasia (BPH), prostate cancer, baldness, acne, obesity and undesirable lipid and steroid profiles in blood and organs.

Approximately 70% of males in the U.S. over the age of 50 have pathological evidence of BPH. Prostate cancer is the second leading cause of cancer death in males in the U.S. Male-patterned baldness can start as early as the teens in genetically susceptible males, and it has been estimated to be present in 30% of Caucasian males at age 30, 40% of Caucasian males at age 40, and 50% of Caucasian males at age 50. Acne is the most common skin disorder treated by physicians. In women, hirsutism is one of the hallmarks of excessive androgen. The ovaries and the adrenal are the major sources of androgen in women.

In men, the major androgen circulating in the blood is testosterone. About 98% of the testosterone in blood is bound to serum proteins (high affinity finding to sex-steroid binding globulin and low affinity binding to albumin), with only 1–2% in free form. The albumin-bound testosterone, the binding of which is readily reversible, and the free form are considered to be bioavailable, and account for about 50% of total testosterone. Testosterone enters target cells apparently by diffusion. In the prostate, seminal vesicles, skin, and some other target organs, it is converted by a NADPH-dependent 5α-reductase to a more active metabolite, 5α-DHT. 5α-DHT then binds an androgen receptor (AR) in target organs. The 5α-DHT-receptor complexes interact with specific portions of the genome to regulate gene activities (Liao et al., 1989). Testosterone appears to bind to the same AR, but it has a lower affinity than 5α-DHT. In tissues such as muscle and testes, where 5α-reductase activity is low, testosterone may be the more active androgen.

The difference between testosterone and 5α-DHT activity in different androgen-responsive tissues is further suggested by findings in patients with 5α-reductase deficiency. Males with 5α-reductase deficiency are born with female-like external genitalia. When they reach puberty, their plasma levels of testosterone are normal or slightly elevated. Their muscle growth accelerates, the penis enlarges, voice deepens, and libido toward females develops. However, their prostates remain non-palpable, they have reduced body hair, and they do not develop acne or baldness.

The findings in 5α-reductase deficient patients suggest that inhibitors of 5α-reductase would be useful for the treatment of prostatic cancer, BPH, acne, baldness, and female hirsutism. Clinical observations and animal experiments have indicated that spermatogenesis, maintenance of libido, sexual behavior, and feedback inhibition of gonadotropin secretion do not require the conversion of testosterone to 5α-DHT. This is in contrast to other hormonal therapies which abolish the actions of both testosterone and 5α-DHT.

Treatment of androgen-dependent skin and prostatic diseases by 5α-reductase inhibitors would be expected to produce fewer side effects than the presently available hormonal therapies. These include castration, estrogen therapy, high doses of superactive gonadotropin-releasing hormone such as Luprolide, and the use of competitive antiandrogens which inhibit AR binding of testosterone and 5α-DHT, such as flutamide, cyproterone acetate and spironolactone. The long term efficacy of competitive antiandrogens is also compromised by their block of the androgenic feedback inhibition of gonadotropin secretion. This increases testicular secretion of testosterone. The higher level of testosterone eventually overcomes the action of the antiandrogen.

Excessive 5α-DHT is implicated in certain androgen-dependent pathological conditions including BPH, acne, male-pattern baldness, and female idiopathic hirsutism. It has been shown that 5α-reductase activity is reported to be higher in hair follicles from the scalp of balding men than that of non-balding men.

Since treatments of androgen-dependent skin and prostatic diseases by 5α-reductase inhibitors can produce fewer side effects than the hormonal therapies which indiscriminately inhibit all androgen actions, it is desirable to provide different types of 5α-reductase inhibitors.

BRIEF SUMMARY OF THE INVENTION

The present invention relates generally to the utilization of certain compounds for the control of androgen activity in target organs and cells through the modulation of a 5α-reductase activity. In certain aspects, these compounds are employed to repress androgenic activity by inhibiting the formation and availability of active androgen in target cells. Consequently, the present invention is useful for the treatment of a wide variety of conditions including, but not limited to, the treatment of prostatic hyperplasia, prostatic cancer, hirsutism, acne, male pattern baldness, seborrhea, and other diseases related to androgen hyperactivity. Several of these compounds have been shown to effectively decrease body weight, and in some cases, to decrease the weight of an androgen-dependent body organ, such as the prostate and other organs. The effectiveness of these compounds may be dependent also on their action on other mechanisms involved in angiogenesis, cell-cell interaction, and on their interaction with various components of organs and cells.

Compounds useful in the practice of the present invention include various isomers of saturated and unsaturated fatty acids, natural and synthetic analogues, and derivatives from which these fatty acids can be generated as well as the metabolites and oxidation products of these fatty acids. The use of these and other fatty acids and their derivatives is also contemplated. Also useful are catechin compounds, particularly, catechins that are structurally similar to epicatechin gallate (ECG) and epigallocatechin gallate (EGCG). EGCG has an additional hydroxyl group on the epicatechin gallate molecule, which has been found to be surprisingly active in modulating several 5α-reductase mediated processes. EGCG derivatives having such an additional OH group on the altering ECG molecule were shown to be active in inducing body weight loss and particularly in reducing the size of androgen sensitive organs such as preputial glands, ventral prostate, dorsolateral prostate, coagulating glands, seminal vesicles, human prostate tumors, and breast tumors in nude mice.

By analogy with the fatty acid compounds, certain active catechin gallates may not enter target cells easily. However, esterification of hydroxyl groups on the inhibitor compounds should enhance the ability of these compounds to enter the target cells. Once inside the cells, esters would be readily hydrolyzed by esterase to alcohols that can inhibit 5α-reductases (Williams, 1985).

In more particular aspects of the invention, the inventors have discovered that certain catechins, particularly EGCG, can be administered to promote body weight loss that differentially affects overall body weight and prostate weight loss. In particular examples, it was shown that for a certain percentage of overall body weight loss, prostate weight loss was percentage-wise more than three times as much. The loss in body weight and the organ weight are likely due to EGCG interference of a common step in the pathway controlling body weight and the organ weight gain. EGCG and related compounds may interact and interfere with a receptor macromolecule (probably containing a protein) that modulates specific lipid synthesis and accumulation. Lipids can modulate gene expression, cell development and differentiation, and organ growth. Specific interference of lipid metabolism in the cells and organs may control the growth of the organs, in particular, prostate, sebaceous, preputial and other secretory organs. In certain applications, it is expected that benign or abnormal growth or cancer of these organs may be treated or even prevented by administration of catechin related compounds.

It has been demonstrated that catechin compounds will arrest or reduce human prostate and breast cancer cell growth. The effectiveness of catechin compounds was shown to be dependent on the methods by which these compounds were administered to the experimental animals. Intraperitoneal application was much more effective than oral administration. It is expected that direct application to the organs, such as the prostate, will be very effective. EGCG was surprisingly effective in suppressing and even reducing the size of human prostate and breast tumors in animal models. The effect was illustrated with EGCG; however, structurally similar catechin compounds are also effective, particularly those that are structurally similar to EGCG in having at least one additional hydroxyl group as compared with ECG. Thus, the EGCG species that contain eight hydroxyl groups is significantly more effective in reducing body weight than is ECG, which contains seven hydroxyl groups. Compounds of this general structure are expected to be particularly effective in chemoprevention and chemotherapy of human prostate cancer. Compounds having a part of structure similar to a part of structure of EGCG are also expected to be effective.

Compounds can be used as antiandrogenic agents through topical or systemic application. A preparation for this purpose can include a carrier, a protectant, an antioxidant (such as vitamin C or E, and various catechins and polyphenols), and other pharmaceutical and pharmacological agents. It is also expected that such compounds can be used in a delivery system (oral, local application, injection, or implantation) involving molecular recognition through which the compounds are delivered to target sites. Such a delivery system may involve, among other methods, liposome techniques or immunological devices.

Natural or synthetic chemicals that can modulate the production or cellular action of receptors and macromolecules are useful in the treatment of abnormalities such as obesity, BPH, prostate cancer, skin diseases, baldness, breast tumors, and hirsutism, which are related to lipid synthesis, body weight, and/or androgen function.

Animal models can be used to demonstrate the effectiveness of compounds on a variety of cancers. For example, Shionogi tumor and other tumors can be studied in male rats. Human breast and prostate cancer cell growth can be studied in nude mice. Alternatively, rodent breast tumors induced by carcinogens and other cancers induced in transgenic mice or Dunning tumor in rats can be similarly analyzed for their chemotherapy by EGCG and related compounds.

The use of compounds disclosed in the present invention, or in natural therapeutically effective amounts of pharmaceutical compositions containing one or more of the compounds, in some cases in combination with other therapeutic agents and carriers, or in natural or synthetic products, is appropriate in the treatment of various disorders. These disorders include, but are not necessarily limited to, those conditions wherein excessive androgenic activities have been implicated, for example, male pattern baldness, female hirsutism, skin disorders, BPH, cancers of prostate, breast, skin and other organs.

The present invention is also directed to novel compounds. These compounds have the formula:

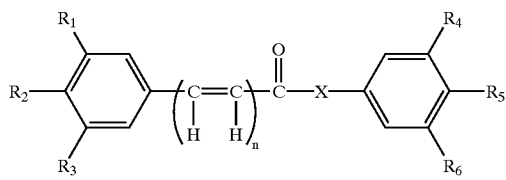

where
  x is —NHCH$_2$CH$_2$— or —CH=CH—;
  R$_1$, R$_2$ and R$_3$ each may be —H, —OH or —OCH$_3$, provided that only one of R$_1$, R$_2$, and R$_3$ may be —H;
  R$_4$, R$_5$ and R$_6$ each may be —H, —OH, —OCH$_3$ or —N(CH$_3$)$_2$, provided that only one of R$_4$, R$_5$ and R$_6$ may be —H; and
  n is 0 or 1.
and the formula:

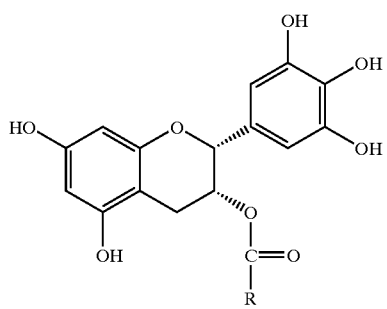

where R is

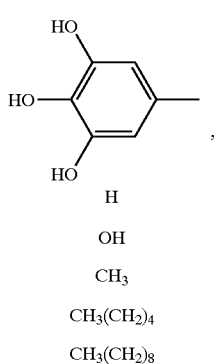

OH
CH$_3$
CH$_3$(CH$_2$)$_4$
CH$_3$(CH$_2$)$_8$

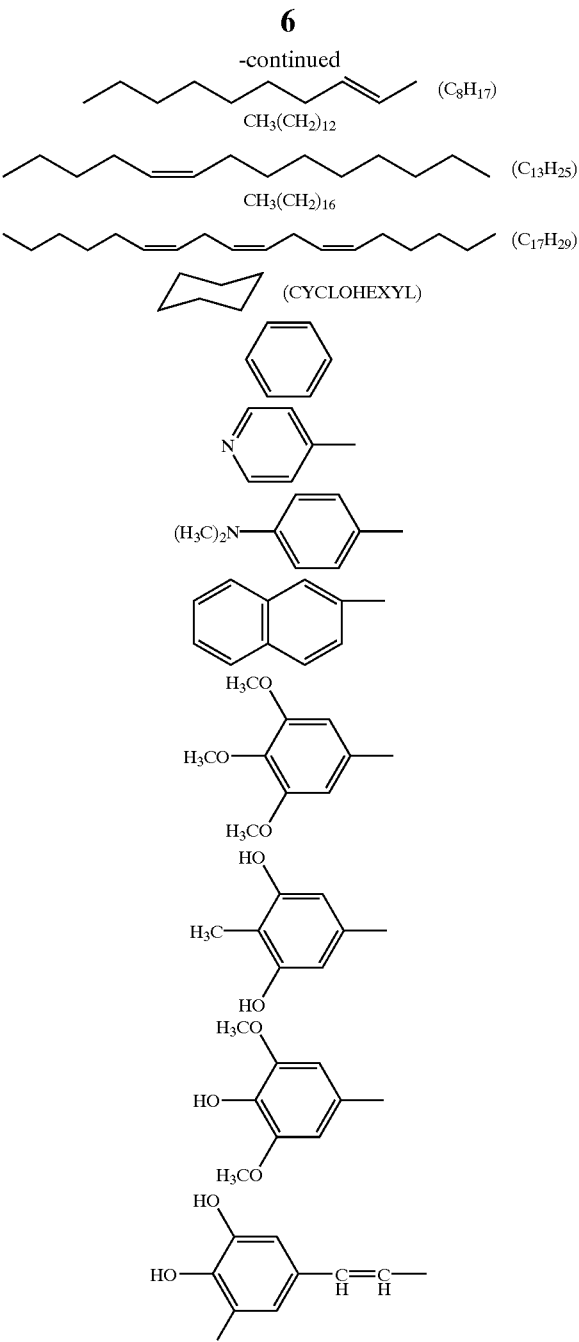

All of the compositions and methods disclosed and claimed herein can be made without undue experimentation in light of the present disclosure. While the compositions and methods of this invention have been described in terms of preferred embodiments, it will be apparent to those of skill in the art that variations may be applied to the compositions, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

BRIEF DESCRIPTION OF THE DRAWINGS

In the drawings, which form a portion of the specification:

FIG. 1 shows the structure of flavanoid compounds of the present invention.

FIG. 2 shows the structure of catechol compounds of the present invention.

FIG. 3 shows the structure of curcumin and related compounds of the present invention.

FIG. 4. shows quinones of the present invention.

FIG. 5 shows epigallocatechin derivative compounds of the present invention.

FIG. 6 shows the generic formula of the epigallocatechin derivatives of the present invention;

FIG. 7 shows the generic formula of gallates useful in the present invention;

FIG. 8 shows the generic formula of curcumin derivatives useful in the present invention;

FIG. 9 shows the generic formula of quinones and catechols useful in the present invention.

FIG. 10 shows fatty acids of the present invention.

DETAILED DESCRIPTION OF THE INVENTION

I. 5α-Reductase Activity

The present invention is concerned with methods of inhibiting 5α-reductase, which include subjecting a cell to an effective concentration of a 5α-reductase inhibitor such as one of the compounds disclosed herein. It is believed that the use of such inhibitors to block abnormal androgen action will serve to treat cancer in conjunction with other anticancer agents, chemotherapy, resection, radiation therapy, and the like. The compounds of this invention, besides acting as 5α-reductase inhibitors, may have other effects that can lead to antitumor activity or to suppress abnormal growth of prostate or other organs.

In mammalian cells, 5α-reductase is very tightly associated with intracellular membranes, including the membrane of the endoplasmic reticulum and contiguous nuclear membranes. Attempts to solubilize and purify active 5α-reductase have not been very successful. The assay of 5α-reductase activity, therefore, is performed by measuring the rate of conversion of testosterone to 5α-DHT by whole cells or by microsomal and nuclear preparations in the presence of NADPH (enzymatic assay). Alternatively, the 5α-reductase activity can be reliably assayed by following NADPH-dependent noncovalent binding of a potent radioactive inhibitor, such as [$^3$H]4-MA ([$^3$H]4-MA-binding assay), which strongly competes with testosterone for binding to the reductase. The results of the two assays correlate very well when microsomal preparations from different organs or animals are used for comparison.

A. [$^3$H]4-MA Binding Assay for 5α-Reductase

Briefly, the binding assay solution, in a final volume of 0.15 ml, contains microsomes (2–20 μg of protein), 0.07 μCi of [$^3$H]4-MA, 0.1 mM-NADPH, 1 mM-dithiothreitol and 50 mM-potassium phosphate, pH 7.0, with or without the indicated amount of a lipid or an inhibitor preparation. Lipids are dissolved in ethanol and added in 1–5 μl volumes. Control tubes receive the same amount of ethanol. After incubation at 0° C. for 1 hour, the [$^3$H]4-MA bound to microsomes is determined by collecting microsomes on a Whatman glass fibre filter and washing with 10 ml of 20 mM-potassium phosphate, pH 7.0, containing 0.01% CHAPS to remove unbound [$^3$H]4-MA.

B. Assays of the Enzymatic Activity of Microsomal 5α-Reductase

The standard reaction mixture, in a final volume of 0.15 ml, contains microsomes, 1, μCi of [$^3$H]testosterone, 0.5–3.0 μM non-radioactive testosterone, 0.1 mM-NADPH, 1 mM-dithiothreitol and 50 mM-potassium phosphate, pH 7.0, with or without the indicated amount of a lipid or an inhibitor preparation. The reaction is started by the addition of microsomes and the incubation is carried out at 37° C. for 15 minutes. Steroids are extracted and separated by thin layer chromatography. Radioactive steroids are located by fluorography and the amount of radioactivity present determined by scintillation counting. The 5α-reductase activity was measured by analyzing the extent of the conversion of [$^3$H]testosterone to [$^3$H]5α-DHT.

C. Sources of 5α-Reductase Activity

Microsomes are prepared at 4° C. from a buffered 0.32 M-sucrose homogenate of human liver and from the livers of adult Sprague-Dawley female rats by differential centrifugation, and are used in the assay of 5α-reductase activity. In some experiments, microsomes are solubilized with 0.1% polyoxyethylene ether W-1, except for the substitution of polyoxyethylene ether W-1 for Lubrolx-WX.

Cells genetically engineered to express specific types of 5α-reductase isozymes can also be used as sources of 5α-reductase activity. Intact cells containing 5α-reductase, their microsomes, or nuclear preparations can also be used to screen 5α-reductase inhibitors.

II. Prostate and Breast Cancer

A compound of this invention can be used to treat breast or prostate cancer. The effectiveness of such compounds against prostate and breast cancer can be determined either on isolated cell lines derived from such cancer tissues or in animals demonstrating these forms of cancer. By way of example, human prostate cancer PC-3 cells are grown in culture medium. About one million cells are injected into male nude mice and the growth of tumors followed. Within two weeks, the tumor grows to about 100 mm$^3$. Three tumor bearing mice are injected with a test compound each day.

III. Organ and Body Weight Loss

A compound of this invention can be used to decrease organ and body weight. The compounds thus have use in treating obesity. The effectiveness of a compound can be determined using well-known animal models.

By way of example, male Sprague-Dawley rats (body weight 180 g±10 g) are used. Compounds are intraperitoneally injected into rats in one group each day for 7 days. Rats in the control group receive 0.1 ml 30% ethanol. Body and organ weights are determined.

IV. Skin Disorders

The inventors sought an inhibitor of 5α-reductase that would be active topically and inactive systemically; such an agent would be ideal for treatment of androgen-dependent dermatological disorders. In this study, inhibition of androgen action by topical administration of γ-LA in hamster flank organs is investigated. Especially useful in the evaluation of the effects of these compounds on skin cells or sebaceous glands is the hamster flank organ (Frost and Gomez, 1972). The paired flank organs, one on each side of the costovertebral angle, are highly sensitive to androgen stimulation. The androgen sensitive structures in the flank organ include dermal melanocytes, sebaceous glands, and hair follicles (Hamilton and Montagna, 1950). This animal model has been widely used for testing androgenic (Hamilton and Montagna, 1950; Frost et al., 1973) and antiandrogenic compounds (Voigt and Hsia, 1973; Weissmann et al., 1985; Chakrabarty et al., 1980). The unique advantage of this animal model is that a testing compound can be applied topically to only one of the flank organs and the effect observed on both organs. If the test compound has only a local effect, then only the treated flank organ is affected. However, if the effect is systemic, then both flank organs are affected.

Pre-pubertal male Syrian golden hamsters, castrated at 4 weeks old, are obtained from Harlan Sprague-Dawley Co. (Madison, Wis.). Each animal is maintained individually in a plastic cage on rodent chow (Purina) and water ad libitum on a 12 hour light/12 hour dark cycle.

One to two weeks after castration, the hair on the lower back of each animal is clipped with an electric hair clipper and then shaved weekly to expose the flank organs. The animals are divided into treatment groups. A treatment solution (5 $\mu$) is applied topically to the right flank organ once a day using a Pipetteman and a polypropylene disposable tip. Unless specified, the left flank organ is not treated. The treatment solution contains either (a) ethanol alone (vehicle and control), or (b) a test compound. The flank organ was wiped with an alcohol pad to remove residual compound before each treatment. At the end of each experiment (17–25 days), the animals were sacrificed by either suffocation with $CO_2$ gas or with an intraperitoneal injection of an overdose of phenobarbital (64.8 mg/ml/animal). The flank organs, both the treated and untreated sides, are evaluated to determine the effect of these treatments on the growth of the pigmented macule and the sebaceous glands. The body weight of each animal is recorded before and after treatment.

Treatment of Animals

Male hamsters, 4 weeks old, are castrated and are kept on a longer light period (16 hours light/8 hours dark cycle) to insure maximum stimulation of sexual characteristics (Luderschmidt et al., 1984). Flank organs, left and right, were treated topically with 5 $\mu$l ethanol containing 0.5 g or 1 $\mu$g testosterone daily. Animals are divided into groups of 4–5 hamsters. The right flank organ is also treated daily with 5 $\mu$l solution containing vehicle (ethanol) alone or test compound (1 or 2 mg) for 18 days. The left flank organ of all animals receives the same volume of vehicle.

the lengths of the long axis and the short axis of the pigmented spot (pigmented macule) are measured using a caliper with digital display (Digimatic, Mitutoyo Corp., Japan). The product (long axis x short axis, mm$^2$) is used as an index of the surface area (Wuest and Lucky, 1989).

The flank organ treated with test compound becomes elevated and palpable. The length of the long axis and short axis of the elevated mass are measured with a caliper. The product of the long axis x short axis (mm$^2$) was used as an index of the areas of the sebaceous gland, which correlates with the volume of the sebaceous glands.

V. Baldness

Topical Effects of Compounds on Hair Loss and Growth

The stumptail macaque monkey develops baldness in a pattern resembling human androgenetic alopecia The balding process begins shortly after puberty (approximately 4 years of age). This occurs in nearly 100% of the animals, males and females, and is androgen dependent. This is a useful animal model for human androgenetic alopecia and is contemplated to be useful in demonstrating the effects of polyunsaturated fatty acids on hair loss. The following describes a protocol for testing.

Male stumptail macaques (4 years of age) are divided into groups of 3 to 5 animals. A defined area of the scalp involving the frontal and vertex areas is marked, e.g., by tattoo. Hairs in the marked area are shaved. The solutions of a test compound in different dosages and combinations are evenly applied to the shaved areas once or twice a day. Control animals receive the same volume of the solvent (e.g., ethanol or other organic solvent, or a cream). The same area of the scalp is shaved every 4 to 6 weeks and the weights of hairs shaved are determined. The treatments may last for 6 months to 2 years. 4-MA (17-N,N-diethylcarbamoyl-4-methyl-4-aza-5-androstan-3-one), a 5$\alpha$-reductase inhibitor known to prevent baldness in this animal is included as a positive control. Biopsies of the scalp (4 mm punch) are obtained before and at the end of the treatments. The specimens are analyzed for 5$\alpha$-reductase activity and examined histologically for evidence of alopecia.

VI. Effects of Compounds on Sebum Productions in a Human Model

Topical antiandrogenic activity of several fatty acids and catechins is first evaluated in the hamster flank organ assay or the rat assay. To further confirm the effectiveness of antiandrogenic compounds and suitability for human use, tests are performed on a human male subject. The ideal compounds for human treatment are those that are topically and locally active but do not show systemic antiandrogenic activity, especially in the cases involving young males.

Determination of Forehead Sebum Production

A male volunteer is used to test and analyze sebum production from the forehead region. The forehead is washed thoroughly with soap twice and then cleaned with 70% isopropyl alcohol twice. Sebum production is measured 30 to 60 minutes later with a sebum meter tape probe (7 mm×8 mm) covering 56 mm$^2$ area in each measurement. Ten measurements are made within the 4 cm square area (16cm$^2$) located at the middle of the left or right side forehead between the eyebrow and the hair line.

The sebum meter detects the difference in the transparency of the tape before and after the tape was placed on the forehead for 30 seconds and expresses the difference in an arbitrary number (S-value) between 0 to 300 (or higher). S-values of sebum accumulated on the foreheads of men are usually 200 to 300. Skin surface on hands usually shows a very low number (5 to 20). The S-value for forehead immediately after washing is less than 5. For men, the S-value gradually increases to about 50 within 30 minutes after washing and reaches 100 to 200 in 45 minutes to 55 minutes.

To determine the rate of sebum production, the left and the right forehead areas are measured alternatively and each time at the comparable areas on the two sides. Ten measurements on each side (i.e., 20 measurements for two sides) take about 15–20 minutes and the sebum-values likely range between 30 to 200. The S-values can differ considerably at different areas of the forehead and could be influenced by environmental, including weather, diet, and physiological, conditions. However, the ratio of the total S-value (the sum of 10 measurements) for the left and the total S-value for the right forehead is constant. Therefore, compounds applied to the left forehead that reduce the L/R ratio to lower than 1.1 are considered as topically active agents for suppression of sebum production.

VII. Pharmaceutical Compositions

Aqueous compositions of the present invention comprise an effective amount of the 5$\alpha$-reductase inhibitory agent dissolved or dispersed in a pharmaceutically acceptable aqueous medium. The phrase "pharmaceutically acceptable" refers to molecular entities and compositions that do not produce an allergic or similar untoward reaction when administered to a human.

The preparation of an aqueous composition that contains such an inhibitory compound as an active ingredient is well understood in the art. Typically, such compositions are prepared as injectable, either as liquid solutions or suspensions; solid forms suitable for solution in, or suspension in, liquid prior to injection can also be prepared. The preparation can also be emulsified.

The pharmaceutical compositions disclosed herein may be orally administered, for example, with an inert diluent or with an assimilable edible carrier, or they may be enclosed in hard or soft shell gelatin capsule, or may be compressed into tablets, or they may be formulated for controlled release, such as a transdermic and osmotic pressure device, injectable device, and implantable device, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. The percentage of the compositions and preparations may, of course, be varied and may conveniently be 100% (application of pure compounds). The amount of active compounds in such therapeutically useful compositions is such that a suitable dosage will be obtained.

The tablets, troches, pills, capsules and the like may also contain the following: a binder, such as gum tragacanth, acacia, corn starch or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin; or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds; sucrose, as a sweetening agent, methyl and propylparabens as preservatives; a dye and flavoring, such as cherry or orange flavor. Of course, any material used in preparing any dosage unit form should be pharmaceutically pure and substantially non-toxic. In addition, the active compounds may be incorporated into sustained-release preparations and formulations.

The active compounds may also be administered parenterally, intravenously, or intraperitoneally. Solutions of the active compounds as a free base or pharmacologically acceptable salts can be prepared in water suitably mixed with a surfactant, such as hydroxypropylcellulose. Dispersions can also be prepared in glycerol, liquified polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such a lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the composition may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The composition can be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formation, solutions will be administered in a manner compatible with the dosage formulation and in such a manner as it therapeutically effective. The formulations are easily administered in a variety of dosage forms such as injectable solutions, drug release capsules and the like.

In other embodiments, one may desire a topical application of compositions disclosed herein. Such compositions may be formulated in creams, lotions, solutions, or in solid form depending upon the particular application. The formulation of pharmaceutically acceptable vehicles for topical administration is well known to one of skill in the art (see, i.e., "Remington's Pharmaceuticals Sciences", 15$^{th}$ Edition). Variation of the dosage of the compositions disclosed herein, will necessarily depend upon the particular subject, and the nature of the condition(s) being treated.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermic or intravenous fluid or injected at the proposed site of infusion, (see, for example, "Remington's Pharmaceutical Sciences", 15$^{th}$ Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

EXAMPLE

Assays for Candidate Substances

Expression of Human 5α-Reductases

For the preparation of rat 1A cells expressing different types of human 5α-reductases, cDNAs for the human type 1 and 2 5α-reductases were isolated from human prostate Ågt11and PC-3 cell ÅZAP II cDNA libraries using the published sequence of the 5α-reductases, PCR and standard library screening techniques. The type 1 and 2 cDNAs were subcloned into the retroviral expression vector pMV7 and high titer stocks of virus containing the type 1 and 2 cDNAs were generated using the packaging cells BOSC 23 293. Rat 1A cells were infected with virus and cells containing integrated retrovirus were selected for G418 resistance (Brown and Scott, 1987).

Assay of 5α-Reductase

Microsomes were prepared from rat 1A cells expressing specific types of human 5α-reductase. The enzymic assay was based on the measurement of 5α-DHT production from testosterone in the presence of microsomes prepared from rat 1A cells containing either the type 1 or type 2 human 5α-reductase. The amount of labeled testosterone and dihydrotestosterone in extracts was determined by thin layer chromatography and scanning on a AMBIS radioanalytic scanner. The concentration of test compound inhibiting the conversion of testosterone to dihydrotestosterone by 50% (IC50) was determined by interpolation between appropriate data points.

Inhibition of 5α-Reductase Activity

Previously, we showed that two natural products, the green tea catechins, epicatechin gallate (ECG) and epigallocatechin gallate (EGCG) and unsaturated fatty acids were inhibitors of human 5α-reductase. A structure-activity relationship study was initiated to explore the structural requirements for this activity. Data for this study are summarized in Tables 1–7 and FIGS. 1–6.

1. Flavanoids

A variety of naturally occurring flavanoids with structures related to the tea catechins were tested (FIG. 1, Table 1).

TABLE 1

| Cell Free Assay Isoenzyme | HRED1 IC50 (uM) | HRED1 % Inhibition @100 uM | HRED2 IC50 (uM) | HRED2 % Inhibition @100 uM |
|---|---|---|---|---|
| Compound | | | | |
| 1. Epicatechin Gallate | 11 | 100 | 60 | 83 |
| 2. Epigallocatechin Gallate | 15 | 99 | 74 | 74 |
| 3. Myricetin | 23 | 96 | >100 | 31 |
| 4. Quercitin | 23 | 96 | >100 | 14 |
| 5. Baicalein | 29 | 79 | 99 | 51 |
| 6. Fisetin | 57 | 97 | >100 | 4 |
| 7. Biochanin a | >100 | 50 | 17 | 74 |
| 8. Kaempferol | >100 | 22 | 12 | 62 |
| 9. Flavone | >100 | 20 | >100 | (−52) |

TABLE 1-continued

| Cell Free Assay Isoenzyme | HRED1 IC50 (uM) | HRED1 % Inhibition @100 uM | HRED2 IC50 (uM) | HRED2 % Inhibition @100 uM |
|---|---|---|---|---|
| Compound | | | | |
| 10. Genistein | >100 | 16 | 23 | 76 |
| 11. Epigallocatechin | >100 | 15 | >100 | 3 |
| 12. Epicatechin | >100 | 14 | >100 | 4 |
| 13. Morin | >100 | 6 | >100 | 33 |
| 14. Alpha-napthoflavone | >100 | 6 | >100 | (−13) |
| 15. Taxifolin | >100 | 5 | >100 | 5 |
| 16. Rutin | >100 | 4 | >100 | 0 |
| 17. Daidzein | >100 | 3 | 29 | 69 |
| 18. Beta-napthoflavone | >100 | 3 | >100 | 4 |
| 19. Chrysin | >100 | 2 | >100 | 1 |

The tea catechins, ECG and EGCG, had the highest activity of the tested flavanoids and were better inhibitors of the type 1 (HRED1) than the type 2 (HRED2) isoenzyme of 5α-reductase. The tea catechins epicatechin (EC) and epigallocatechin (EGC) had little activity. Four flavanoids, myricetin, quercitin, baicalein and fisetin had significant (IC50<100 μM) activity and were more active against the type 1 than the type 2 isoenzyme. Biochanin A, kaempferol, genistein, and diadzein were effective inhibitors of the type 2 but not type 1 isoenzyme. Comparison of the activities of chrysin, kaempferol, morin, myricetin, and quercitin indicate the importance of B-ring hydroxyl groups, especially in a catechol or pyrogallol configuration, and perhaps the importance of the hydroxyl at position 3 for activity against the type 1 isozyme. Rutin, the 3-rutinose glycoside of quercitin was ineffective against either isoenzyme (IC50>100 μM). The inactivity of rutin compared to quercitin is either due to the presence of the oligosaccharide rutinose (perhaps due to steric hindrance) or modification of the hydroxyl at position 3. Taxifolin, a flavanone, was ineffective against either isozyme (IC50>100 μM). The weak activity of taxifolin is most likely due to the absence of the 2,3-unsaturated bond when its activity is compared to the structurally related quercitin. When tested for inhibitory activity in whole cells, most flavanoids showed little or no activity against the type 1 isoenzyme, perhaps indicating limited penetration of these polyhydroxy compounds across the cell membrane. In contrast to the results with the type 1 enzyme, four flavanoids, biochanin A, diadzein, kaempferol and genistein had significant inhibitory activity against the type 2 isoenzyme in the whole cell assay. The most active of these, biochanin A and diadzein, have only two and three free hydroxyl groups, respectively, and so may penetrate cells easier than other flavanoids.

2. Catechols

5α-reductase inhibition studied with the flavanoids indicated the potential importance of catechol and pyrogallol moieties for high inhibitory activity. Therefore, a series of compounds with catechol groups was surveyed for activity (Table 2, FIG. 2).

TABLE 2

| Cell Free Assay Isoenzyme | HRED1 IC50 (uM) | HRED1 % Inhibition @100 uM | HRED2 IC50 (uM) | HRED2 % Inhibition @100 uM |
|---|---|---|---|---|
| Compound | | | | |
| 1. Anthrarobin | 4 | 99 | 50 | 97 |
| 2. Bromopyrogallol Red | 7 | 98 | 84 | 58 |

TABLE 2-continued

| Cell Free Assay Isoenzyme | HRED1 IC50 | HRED1 % Inhibition | HRED2 IC50 | HRED2 % Inhibition |
|---|---|---|---|---|
| Compound | (uM) | @100 uM | (uM) | @100 uM |
| 3. Gossypol | 7 | 99 | 21 | 99 |
| 4. Pyrogallol Red | 15 | 97 | >100 | 27 |
| 5. Nordihydrogaiaretic Acid | 19 | 99 | 50 | 80 |
| 6. Caffeic Acid Phenethyl Ester | 26 | 97 | >100 | 36 |
| 7. Octyl Gallate | 27 | 99 | 58 | 90 |
| 8. Purpurogallin | 30 | 81 | >100 | 31 |
| 9. Hydroxydopamine | 42 | 69 | >100 | 41 |
| 10. Dodecylgallate | 43 | 88 | >100 | 36 |
| 11. Pyrocatechol Violet | 48 | 85 | 100 | 47 |
| 12. Pyrogallol | 70 | 60 | >100 | 28 |
| 13. Hematoxylin | 83 | 59 | >100 | 38 |
| 14. HZIV-82 | >100 | 43 | >100 | 0 |
| 15. Cnc | >100 | 42 | >100 | (−75) |
| 16. HZIV 90 | >100 | 23 | >100 | 13 |
| 17. Caffeic Acid | >100 | 13 | >100 | 8 |
| 18. HZIV 275 | >100 | 10 | >100 | 6 |
| 19. Exculetin | >100 | 7 | >100 | 13 |
| 20. Ellagic Acid | >100 | 7 | >100 | 9 |
| 21. Catechol | >100 | 5 | >100 | 0 |
| 22. Methylgallate | >100 | 5 | >100 | 3 |
| 23. Fraxetin | >100 | 2 | >100 | 8 |
| 24. Propylgallate | >100 | 0 | >100 | 0 |

Thirteen of the 24 compounds listed had IC50's below 100 μM. All were more active against the type 1 than type 2 isoenzyme. Six of these compounds, anthrarobin, dodecyl gallate, gossypol, octyl gallate, caffeic acid phenethyl ester and nordihydroguaiaretic acid were active in whole cell assays (Table 7, below). Anthrarobin was much more effective against the type 1 than type 2 isoenzyme; whereas, the other five inhibitors were equally effective inhibitors of both isoenzymes. The synthetic compound HZIV 82 showed little activity in the cell-free assay, but was very active in the whole cell assay with specificity for the type 1 isoenzyme.

3. Curcumin and Related Compounds

Curcumin was a very effective inhibitor of either the type 1 or type 2 isoenzyme (Table 3, FIG. 3).

TABLE 3

| Cell Free Assay Isoenzyme | HRED1 IC50 | HRED1 % Inhibition | HRED2 IC50 | HRED2 % Inhibition |
|---|---|---|---|---|
| Compound | (uM) | @100 uM | (uM) | @100 uM |
| 1. Curcumin | 3 | 95 | 5 | 87 |
| 2. Tetrahydrocurcumin | 80 | 56 | 29 | 73 |
| 3. Demethoxy-tetrahydrocurcumin | >100 | 23 | >100 | 42 |
| 4. 4-hydroxy-3-methoxy-cinnamaldehyde | >100 | 10 | >100 | (+60) |
| 5. Coniferol | >100 | 10 | 100 | 49 |
| 6. 4-(4-hydroxy-3-methoxyphenol)-3-buten-2-one | >100 | 3 | >100 | 4 |
| 7. Ferulic Acid | >100 | 0 | >100 | 18 |
| 8. Capsaicin | >100 | 0 | >100 | 8 |
| 9. Eugenol | >100 | 0 | 100 | 50 |

Commercially available curcumin was chemically reduced with Pt/H2 and the products, tetrahydrocurcumin and demethoxytetrahydrocurcumin, had much less activity than curcumin. However, tetrahydrocurcumin (HZIV 81–2), which is colorless compared to the bright yellow curcumin, had significant activity in the whole cell assay. The structurally related compounds 4-(4-hydroxy-3-methoxyphenol)-3-buten-2-one, ferulic acid, capsaicin, eugenol and coniferyl alcohol had little inhibitor activity (IC50>100 μM) against either isoenzyme highlighting the importance of the diferulolyl structure for activity against 5α-reductase. Nordihydroguaiaretic acid (NDGA) was also an effective inhibitor of the type 1 (IC50=19 μM) and type 2 (IC50=50 μM) isozymes in cell-free and whole cell assays, but less so than curcumin.

4. Quinones

A variety of quinones were tested for activity against 5α-reductase (Table 4, FIG. 4).

TABLE 4

| Cell Free Assay Isoenzyme | HRED1 IC50 | HRED1 % Inhibition | HRED2 IC50 | HRED2 % Inhibition |
|---|---|---|---|---|
| Compound | (uM) | @100 uM | (uM) | @100 uM |
| 1. Purpurin | 2 | 95 | >100 | 20 |
| 2. Alizarin | 3 | 95 | 100 | 54 |
| 3. Anthrarobin | 4 | 99 | 50 | 97 |
| 4. Menadione | 6 | 77 | 5 | 81 |
| 5. Coenzyme q | 12 | 77 | 22 | 81 |
| 6. 2,5-dichloroindophenol | 15 | 78 | 17 | 97 |
| 7. Alizarin Red 5 | 30 | 91 | >100 | 8 |
| 8. Anthrarufin | 40 | 67 | >100 | 13 |
| 9. Anthrarufin | 40 | 67 | >100 | 13 |
| 10. Lapachol | >100 | 30 | >100 | 9 |
| 11. Anthraflavic Acid | >100 | 27 | >100 | 22 |
| 12. Quinizarin | >100 | 26 | >100 | 7 |
| 13. T-butyl-hydroxyquinone | >100 | 19 | >100 | 4 |
| 14. Anthraquinone | >100 | 6 | >100 | 9 |

The naturally occurring anthraquinone, alizarin, was a very effective inhibitor of the type 1 but not type 2 isozymes. Alizarin Red S, which is a water soluble sulfate derivative of alizarin had little activity (IC50s>100 μM) against either isoenzyme. The charged sulfate group may prevent interaction with membrane bound 5α-reductase. Purpurin, which has an additional hydroxyl compared to alizarin, had inhibitory activity similar to alizarin. Anthraflavic acid, anthrarufin and quinizarin, which are structural isomers of alizarin without adjacent hydroxyl groups, had much less activity, emphasizing the importance of the catechol moiety for potent inhibitory activity of this class of anthroquinones. Anthraquinone was not an effective inhibitor (IC50>100 μM). Menadione, coenzyme Q, and 2,6-dichloroindophenol were potent cell-free inhibitors of boh isoenzymes. The compounds participate in quinone reductase reactions and may deplete NADPH causing the observed inhibition. In the whole cell assay, alizarin was a very effective inhibitor of the type 1 isoenzyme and menadione had moderate activity.

5. Epigallocatechin Derivatives

The high inhibitory activity of EGCG in a cell-free assay but low in the whole cell assay led us to design and synthesize a series of derivatives of EGC to enhance activity in the whole cell assay (Table 5, FIG. 5).

TABLE 5

| Cell Free Assay Isoenzyme | HRED1 IC50 (uM) | HRED1 % Inhibition @100 uM | HRED2 IC50 (uM) | HRED2 % Inhibition @100 uM |
|---|---|---|---|---|
| Compound | | | | |
| 1. EGCG | 12 | 99 | 73 | 76 |
| 2. HZIV 160 | 29 | 99 | 76 | 96 |
| 3. HZIV 134 | 20 | 99 | 67 | 94 |
| 4. HZIV 92 | 23 | 98 | >100 | 45 |
| 5. HZIV 120 | 23 | 99 | 66 | 97 |
| 6. HZIV 142 | 25 | 97 | 63 | 93 |
| 7. HZIV 68 | 29 | 93 | 99 | 51 |
| 8. HZIV 75 | 29 | 97 | >100 | 21 |
| 9. HZIV 166 | 30 | 98 | 78 | 74 |
| 10. HZIV 63 | 311 | 94 | >100 | 20 |
| 11. HZIV 169 | 47 | 90 | >100 | 39 |
| 12. HZIV 74 | 48 | 85 | >100 | 24 |
| 13. HZIV 144 | 49 | 88 | >100 | 38 |
| 14. HZIV 168 | 49 | 98 | 73 | 92 |
| 15. HZIV 166 | 59 | 95 | 71 | 84 |
| 16. BGC | 62 | 61 | >100 | 30 |
| 17. HZIV 107 | 98 | 52 | >100 | 39 |
| 18. HZIV 145 | >100 | 35 | >100 | 8 |
| 19. HZIV 148 | >100 | 31 | >100 | 0 |
| 20. HZIV 109 | >100 | 17 | >100 | 0 |

The studies showed that derivatization of the hydroxyl groups of EGCG with methyl or acetate groups leads to the loss of inhibitory activity in the cell-free assay and no enhancement of the lower whole cell assay inhibitory activity. We, therefore, limited structure-activity studies to changes in the gallate ester moiety of EGCG to enhance inhibitory activity in the whole cell assay. Twenty of these structural changes are summarized in Table 5. The most significant structural change leading to activity in the whole cell assay was introduction of fatty acid ester in place of the gallic acid group of EGCG. In particular, fatty acids with some degree of unsaturation had good inhibitory activity against both isoenzymes of 5α-reductase in the whole cell assay. The most potent of these derivatives was one with γ-linolenic acid esterified to the 3-hydroxyl of EGC. Certain fatty acids with a single unsaturated bond were also active. For example, HZIV 160, the myristoleic ester of EGC was effective in both assay systems. Fatty acids with less unsaturation are less susceptible to oxidation and so may be more suitable modifying agents.

TABLE 6

| Cell Free Assay Isoenzyme | HRED1 IC50 (uM) | HRED1 % Inhibition @100 uM | HRED2 IC50 (uM) | HRED2 % Inhibition @100 uM |
|---|---|---|---|---|
| Compound | | | | |
| 1. Gamma-Linolenic Acid C 18:3 CIS 6,9,12 | 5 | 99 | 11 | 89 |
| 2. Crocetin | 7 | 70 @ 30 | >100 | 20 @ 30 |
| 3. Alpha-Linolenic Acid C 18:3 CIS 9,12,15 | 8 | 99 | 9 | 84 |
| 4. Linoleic Acid C 18:2 CIS 9,12 | 9 | 99 | 19 | 85 |
| 5. Oleic Acid C 18:1 CIS 9 | 10 | 99 | 42 | 86 |
| 6. Conjugated Octadecadienonic Acid | 10 | 99 | 30 | 81 |
| 7. 5,8,11,14-Eocpsatetraynoic Acid | 15 | 97 | 3 | 81 |
| 8. Stearic Acid C 18:0 | 27 | 71 | >100 | 35 |

TABLE 7

| Whole Cell Assay Isoenzyme | HRED1 IC50 (uM) | HRED1 % Inhibition @100 uM | HRED2 IC50 (uM) | HRED2 % Inhibition @100 uM |
|---|---|---|---|---|
| Compound | | | | |
| 1. HZIV 82 | 3 | 79 | >100 | 15 |
| 2. Dodecylgallate | 3 | 99 | 7 | 98 |
| 3. Anthrarobin | 6 | 91 | >100 | 31 |
| 4. Alizarin | 6 | 75 | >100 | 27 |
| 5. Gossypol | 7 | 100 | 6 | 99 |
| 6. HZIV 160 | 7 | 99 | 8 | 98 |
| 7. Octyl Gallate | 7 | 99 | 18 | 94 |
| 8. Caffeic Acid Phenethyl Ester | 8 | 99 | 7 | 98 |
| 9. HZIV 142 | 8 | 99 | 14 | 98 |
| 10. Curcumin | 9 | 99 | 7 | 99 |
| 11. Nordihydro-guaiaretic Acid | 19 | 99 | 22 | 99 |
| 12. HZIV 165 | 28 | 97 | 32 | 98 |
| 13. HZIV 168 | 28 | 93 | 41 | 94 |
| 14. HZIV 81-2 | 36 | 81 | 7 | 92 |
| 15. HZIV 148 | 42 | 90 | 74 | 81 |
| 16. HZIV 75 | 43 | 83 | 62 | 72 |
| 17. HZIV 120 | 49 | 97 | 57 | 96 |
| 18. Menadione | 51 | 82 | 79 | 62 |
| 19. HZIV 166 | 58 | 89 | 72 | 83 |
| 20. Biochanin A | 64 | 64 | 5 | 93 |
| 21. HZIV 92 | 64 | 94 | 80 | 62 |
| 22. Kaempferol | 79 | 60 | 20 | 85 |
| 23. Daidzein | 10 | 13 | 7 | 89 |
| 24. Baicalein | >100 | 24 | >100 | 4 |
| 25. Fisetin | >100 | 42 | >100 | 27 |
| 26. EGCG | >100 | 11 | >100 | 5 |
| 27. Myricetin | >100 | 11 | >100 | 11 |
| 28. Purpurin | >100 | 47 | >100 | 7 |
| 29. Quercetin | >100 | 15 | >100 | 29 |
| 30. Alizarin Red S | >100 | 28 | >100 | 1 |
| 31. Genistein | >100 | 22 | 20 | 89 |
| 32. HZIV 123 | >100 | 48 | >100 | 8 |
| 33. HZIV 107 | >100 | 23 | >100 | 2 |
| 34. Catechol | >100 | 9 | >100 | 3 |
| 35. Daidzein | >100 | 9 | 58 | 87 |
| 36. Pyrogallol | >100 | 7 | >100 | 15 |
| 37. EC | >100 | 0 | >100 | 1 |
| 38. EGC | >100 | 15 | >100 | 1 |
| 39. ECG | >100 | 0 | >100 | 0 |
| 40. EGCG | >100 | 6 | >100 | 0 |
| 41. HZIV 90 | >100 | 34 | >100 | 14 |
| 42. HZIV 63 | >100 | 12 | >100 | 7 |
| 43. HZIV 68 | >100 | 40 | >100 | 34 |
| 44. HZIV 144 | >100 | 12 | >100 | 7 |
| 45. HZIV 81-3 | >100 | 28 | 19 | 80 |
| 46. HZIV 145 | >100 | 8 | >100 | 9 |
| 47. Methyl Gallate | >100 | 0 | >100 | 0 |
| 48. Propyl Gallate | >100 | 5 | >100 | 0 |
| 49. Isopropyl Gallate | >100 | 0 | >100 | 0 |
| 50. Gallic Acid | >100 | 13 | >100 | 0 |
| 51. Pyrogallol | >100 | 5 | >100 | 6 |
| 52. HZIV 169 | >100 | 10 | >100 | 0 |
| 53. Gamma-Linolenic | 22 | 91 | 20 | 86 |
| 54. Etya | 22 | 67 | 2 | 86 |
| 55. Alpha-Linolenic | 29 | 82 | 23 | 86 |
| 56. Linoleic | 40 | 78 | 25 | 77 |
| 57. Oleic Acid | 83 | 58 | >100 | 45 |

TABLE 7-continued

| Whole Cell Assay Isoenzyme | HRED1 IC50 (uM) | HRED1 % Inhibition @100 uM | HRED2 IC50 (uM) | HRED2 % Inhibition @100 uM |
|---|---|---|---|---|
| Compound | | | | |
| 58. Stearic Acid | >100 | 10 | >100 | 23 |
| 59. Alpha-Linolenic Acid Me Ester | >100 | 24 | >100 | 18 |
| 60. Gamma-Linolenic Acid Chol Ester | >100 | 12 | >100 | 11 |
| 61. Gamma-Linolenic Acid Me Ester | >100 | 49 | >100 | 26 |

As found previously in our lab, the greater the degree of unsaturation, the better the inhibitory activity of the fatty acid. Since unsaturated fatty acids are easily prone to oxidation which may comprise their usefulness, we examined some unsaturated fatty acids less prone to oxidation. The synthetic fatty acids, conjugated octadecadienoic acid (CODA) (cis or trans- 9,11 or 10,12 octadecadienoic acid) and 5,8,11,14-eicosatetraynoic acid (ETYA), were good inhibitors of both isoenzymes. CODA and ETYA had IC50s of 10 and 15 (type 1) and 30 and 3 (type 2) $\mu M$, respectively. The naturally occurring fatty acid, γ-linolenic acid, has IC50 of 3 $\mu M$ for both isoenzymes. Fatty acids such as ETYA may be useful for derivatizing other 5α-reductase inhibitors to enhance cellular uptake and promote in vivo activity of 5α-reductase inhibitors. Methyl and cholesterol esters of γ-linolenic acid had little activity in the whole cell assay (TABLE 7) and so the activity of EGC esterified to γ-linolenic acid is unlikely due to intracellular hydrolysis of these esters.

Active 5α-reductase inhibitors shown in Tables 1–7 are polyphenols or their derivatives and are easily oxidized or hydrolyzed within several hours to several days, especially in the presence of air or oxygen and at a pH above 7.0. We have found that these compounds are more stable to oxidation or hydrolysis by maintaining the pH of the solutions of these compounds at a pH below 7.0. More than 80% of the oxidation of hydrolysis can be prevented by the addition of an inorganic acid, such as hydrochloric acid, sulfuric acid, or phosphoric acid, or an organic acid, such as citric acid or acetic acid.

The references listed below and cited in the disclosure are:

1. Anderson and Liao. Nature, 219: 277–279, 168.
2. Brown and Scott, DNA Cloning, A Practical Approach, Vol. III; 189–212, 1987.
3. Bruchovsky and Wilson. J. Biol. Chem 243: 5953–5960, 1968.
4. Chakrabarry et al., J. Invest. Dermatol, 74: 5–8, 1980.
5. Diani et al., J. Clin. Endocrinol. Metab. 74: 345–350, 1992.
6. Frost and Gomez, Adv. Biol. Skin, 12:403–442, 1972.
7. Frost et al., J. Invest. Dermatol, 61:159–167, 1973.
8. Hamilton and Montagna, Amer. J. Anat., 86:191–233, 1950.
9. Hiipakka et al., J. Steroid Biochem. Molec. Biol., 45: 539–548.
10. Hirsch et al., Proc. Natl. Acad. Sci. USA, 90: 5277–5281, 1993.
11. Liang and Liao, Biochem. J. 285: 557–562, 1992.
12. Liang and Liao, J. Invest. Dermatol. 109: 152–157, 1997.
13. Liang et al., Endocrinology 112: 1460–1468, 1983.
14. Liao and Hiipakka, Biophys. Biochem. Res. Commun. 214: 833–838, 1995.
15. Liao et al., J. Steroid Biochem, 34: 41–51, 1989.
16. Liao et al., Cancer Letters, 96: 239–243, 1995.
17. Luderschmidt et al., J. Invest. Dermatol., 83: 157–160, 1984.
18. Randall, Clin. Endrocrinol 40: 439–457, 1994.
19. Russell and Wilson, Ann. Rev. Biochem. 63: 25–61, 1994.
20. Stoner et al., J. Urol. 147: 1298–1302, 1992.
21. Takayasu et al., Endocrinology 90: 73–79, 1972.
22. Voight and Hsia, Endocrinology, 92: 1216–1222, 1973.
23. Weissmann et al., J. Invest. Dermatol., 82: 522–525, 1985.
24. Williams, Clin. Pharmacokinetics, 10: 392–403, 1985.
25. Wuest and Lucky, Skin Pharmacol., 2: 103–113, 1989.

What is claimed is:

1. A process of inhibiting 5α-reductase activity comprising the step of exposing 5α-reductase to an effective inhibiting amount of a compound selected from the group consisting of Myricetin, Quercitin, Baicalein, Fisetin, Kaempferol, Anthrarobin, Bromopyrogallol Red, Gossypol, Pyrogallol Red, Nordihydrogaiaretic Acid, Caffeic Acid Phenethyl Ester, Octyl Gallate, Purpurogallin, Hydroxydopamine, Dodecylgallate, Pyrocatechol Violet, Pyrogallol, Hematoxylin,

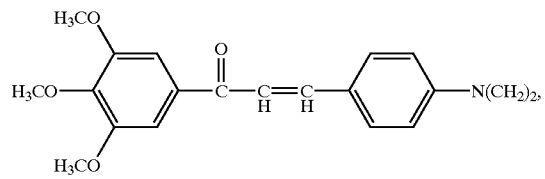

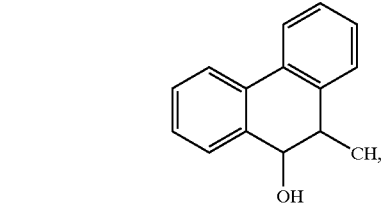

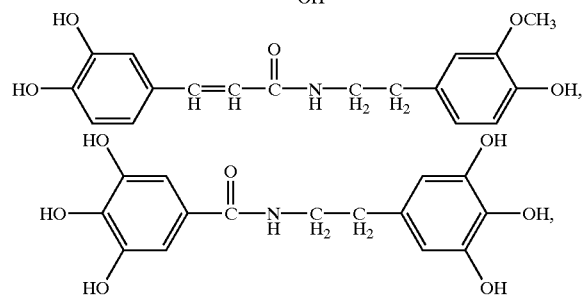

Curcumin, Tetrahydrocurcumin, Purpurin, Alizarin, Menadione, Coenzyme q, 2,5-dichloroindophenol, Anthrarufin, Lapachol, Crocetin, 5,8,11,14-Ecostetraynoic Acid, Nordihydroguaiaretic Acid,

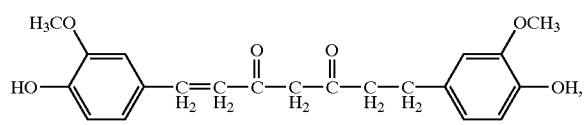

Alizarin Red S, Isopropyl Gallate, and Gallic Acid.

2. A process of treating prostate cancer in a subject in need of such treatment comprising the step of administering to the subject an effective therapeutic amount of a compound selected from the group consisting of Myricetin, Quercitin, Baicalein, Fisetin, Kaempferol, Anthrarobin, Bromopyrogallol Red, Gossypol, Pyrogallol Red, Nordihydrogaiaretic Acid, Caffeic Acid Phenethyl Ester, Octyl Gallate, Purpurogallin, Hydroxydopamine, Dodecylgallate, Pyrocatechol Violet, Pyrogallol, Hematoxylin,

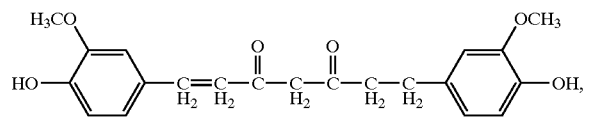

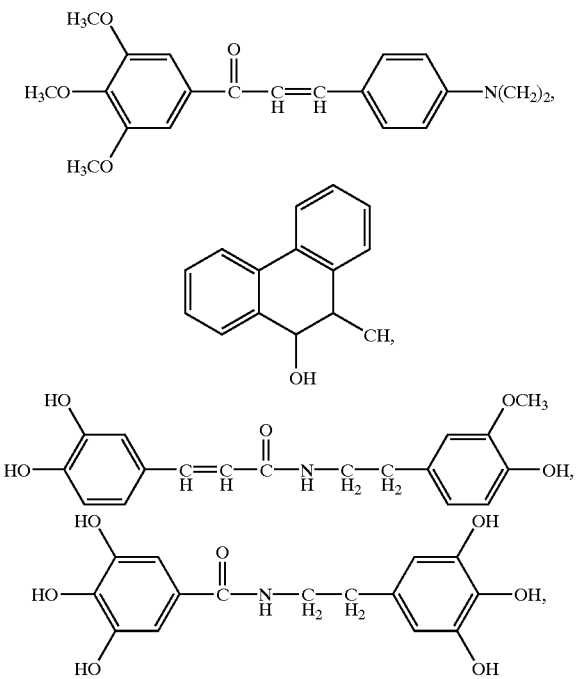

Curcumin, Tetrahydrocurcumin, Purpurin, Alizarin, Menadione, Coenzyme q, 2,5-dichloroindophenol, Anthrarufin, Lapachol, Crocetin, 5,8,11,14-Ecostetraynoic Acid, Nordihydroguaiaretic Acid,

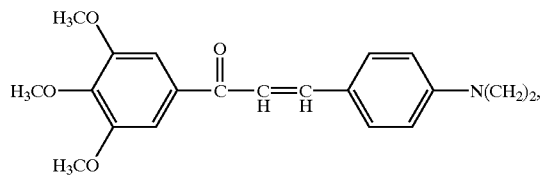

Alizarin Red S, Isopropyl Gallate, and Gallic Acid.

3. A process of treating breast cancer in a subject in need of such treatment comprising the step of administering to the subject an effective therapeutic amount of a compound selected from the group consisting of Myricetin, Quercitin, Baicalein, Fisetin, Kaempferol, Anthrarobin, Bromopyrogallol Red, Gossypol, Pyrogallol Red, Nordihydrogaiaretic Acid, Caffeic Acid Phenethyl Ester, Octyl Gallate, Purpurogallin, Hydroxydopamine, Dodecylgallate, Pyrocatechol Violet, Pyrogallol, Hematoxylin,

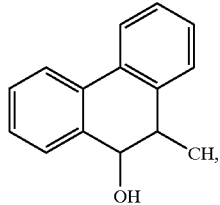

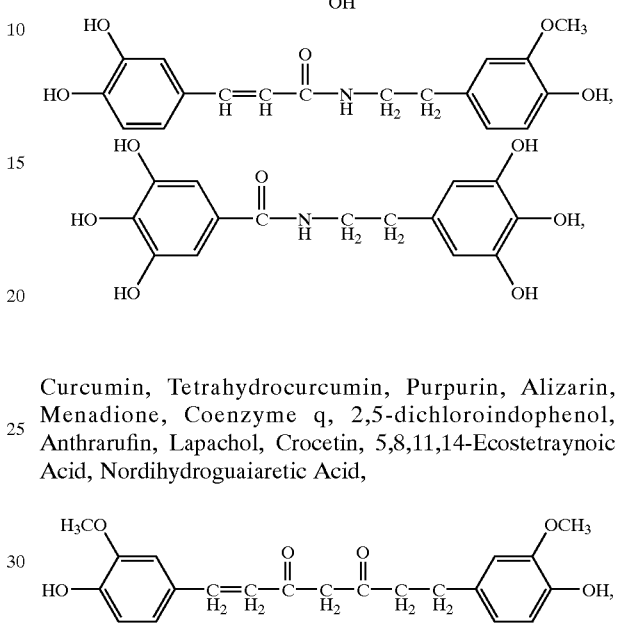

Curcumin, Tetrahydrocurcumin, Purpurin, Alizarin, Menadione, Coenzyme q, 2,5-dichloroindophenol, Anthrarufin, Lapachol, Crocetin, 5,8,11,14-Ecostetraynoic Acid, Nordihydroguaiaretic Acid,

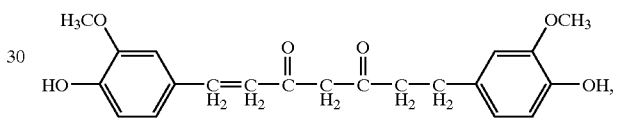

Alizarin Red S, Isopropyl Gallate, and Gallic Acid.

4. A process of treating baldness in a subject in need of such treatment comprising the step of administering to the subject an effective therapeutic amount of a compound selected from the group consisting of Myricetin, Quercitin, Baicalein, Fisetin, Kaempferol, Anthrarobin, Bromopyrogallol Red, Gossypol, Pyrogallol Red, Nordihydrogaiaretic Acid, Caffeic Acid Phenethyl Ester, Octyl Gallate, Purpurogallin, Hydroxydopamine, Dodecylgallate, Pyrocatechol Violet, Pyrogallol, Hematoxylin,

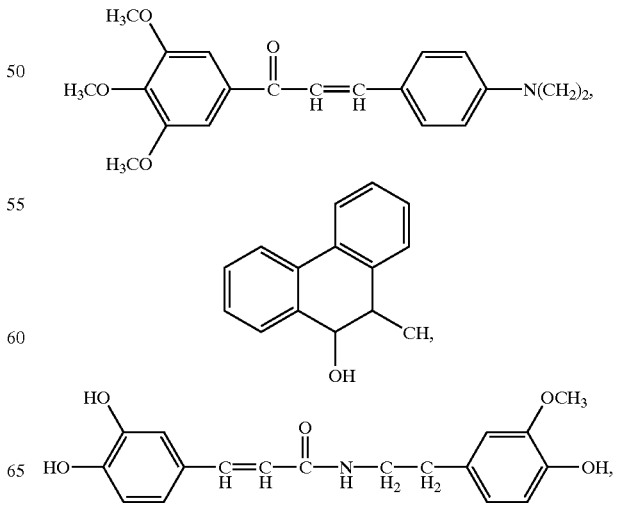

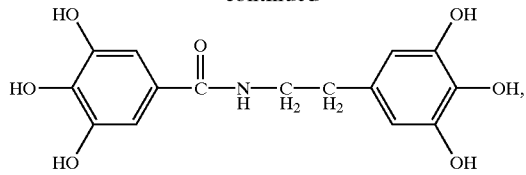

Curcumin, Tetrahydrocurcumin, Purpurin, Alizarin, Menadione, Coenzyme q, 2,5-dichloroindophenol, Anthrarufin, Lapachol, Crocetin, 5,8,11,14-Ecostetraynoic Acid, Nordihydroguaiaretic Acid,

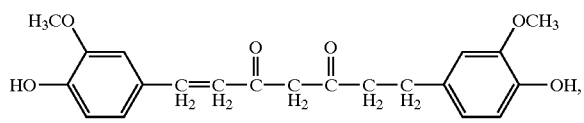

Alizarin Red S, Isopropyl Gallate, and Gallic Acid.

5. A process of treating a skin disorder in a subject in need of such treatment comprising the step of administering to the subject an effective therapeutic amount of a compound selected from the group consisting of Myricetin, Baicalein, Anthrarobin, Bromopyrogallol Red, Gossypol, Pyrogallol Red, Nordihydrogaiaretic Acid, Caffeic Acid Phenethyl Ester, Octyl Gallate, Purpurogallin, Hydroxydopamine, Dodecylgallate, Pyrocatechol Violet, Pyrogallol, Hematoxylin,

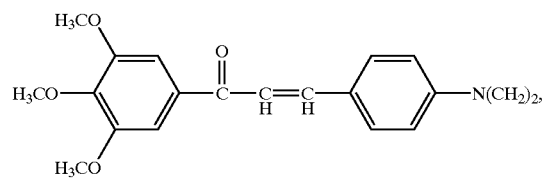

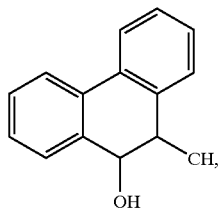

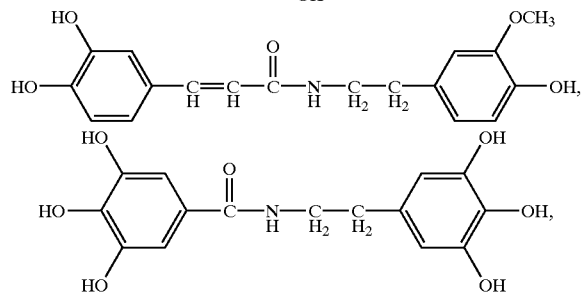

Curcumin, Tetrahydrocurcumin, Purpurin, Alizarin, Menadione, Coenzyme q, 2,5-dichloroindophenol, Anthrarufin, Lapachol, Crocetin, 5,8,11,14-Ecostetraynoic Acid, Nordihydroguaiaretic Acid,

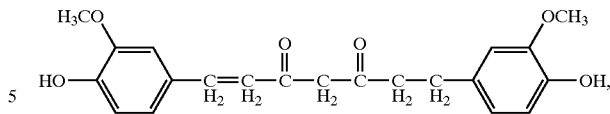

Alizarin Red S, Isopropyl Gallate, and Gallic Acid.

6. A process of treating obesity in a subject in need of such treatment comprising the step of administering to the subject an effective therapeutic amount of a compound selected from the group consisting of Myricetin, Quercitin, Baicalein, Fisetin, Kaempferol, Anthrarobin, Bromopyrogallol Red, Gossypol, Pyrogallol Red, Nordihydrogaiaretic Acid, Caffeic Acid Phenethyl Ester, Octyl Gallate, Purpurogallin, Hydroxydopamine, Dodecylgallate, Pyrocatechol Violet, Pyrogallol, Hematoxylin,

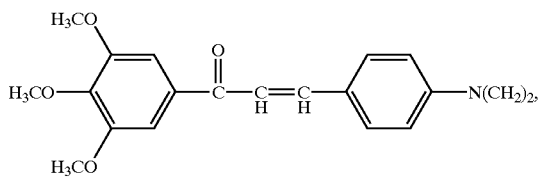

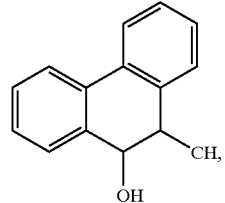

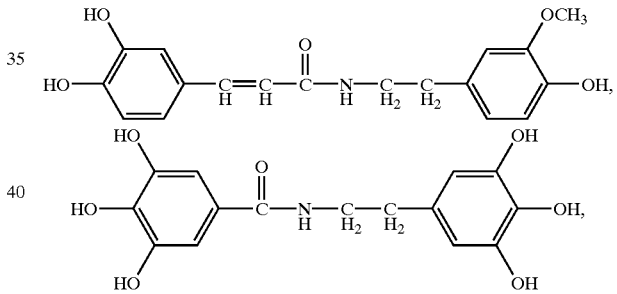

Curcumin, Tetrahydrocurcumin, Purpurin, Alizarin, Menadione, Coenzyme q, 2,5-dichloroindophenol, Anthrarufin, Lapachol, Crocetin, 5,8,11,14-Ecostetraynoic Acid, Nordihydroguaiaretic Acid,

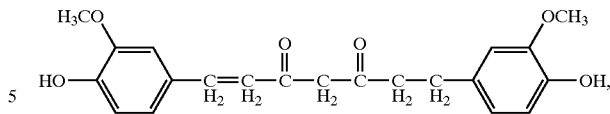

Alizarin Red S, Isopropyl Gallate, and Gallic Acid.

7. A process of treating benign prostatic hyperplasia or prostatitis in a subject in need of such treatment comprising the step of administering to the subject an effective therapeutic amount of a compound selected from the group consisting of Myricetin, Quercitin, Baicalein, Fisetin, Kaempferol, Anthrarobin, Bromopyrogallol Red, Gossypol, Pyrogallol Red, Nordihydrogaiaretic Acid, Caffeic Acid Phenethyl Ester, Octyl Gallate, Purpurogallin, Hydroxydopamine, Dodecylgallate, Pyrocatechol Violet, Pyrogallol, Hematoxylin,

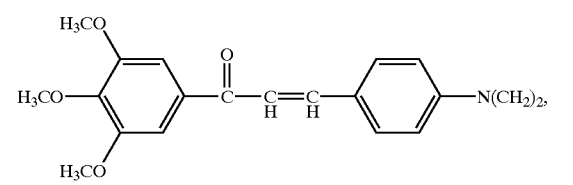

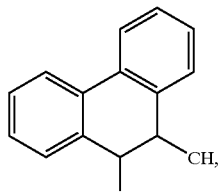

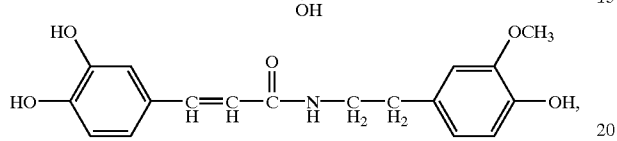

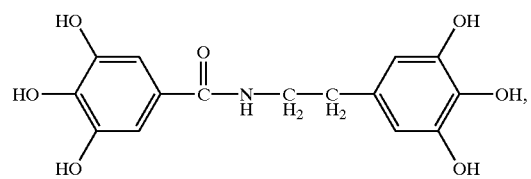

Curcumin, Tetrahydrocurcumin, Purpurin, Alizarin, Menadione, Coenzyme q, 2,5-dichloroindophenol, Anthrarufin, Lapachol, Crocetin, 5,8,11,14-Ecostetraynoic Acid, Nordihydroguaiaretic Acid,

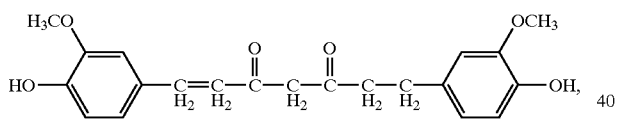

Alizarin Red S, Isopropyl Gallate, and Gallic Acid.

8. A compound of the formula:

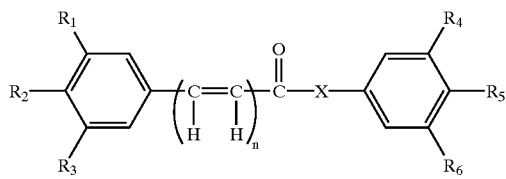

where x is —NHCH$_2$CH$_2$— or —CH=CH—;

R$_1$, R$_2$ and R$_3$ each may be —H, —OH or —OCH$_3$, provided that only one of R$_1$, R$_2$, and R$_3$ may be —H;

R$_4$, R$_5$ and R$_6$ each may be —H, —OH, —OCH$_3$ or —N(CH$_3$)$_2$, provided that only one of R$_4$, R$_5$ and R$_6$ may be —H; and n is 0 or 1.

9. A compound of the formula:

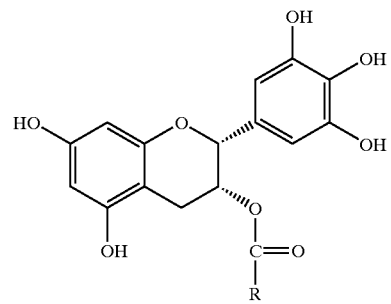

where R is a chain with 2 to 20 atoms from the group consisting of carbon, oxygen, sulfur, and nitrogen, without or with one to four double bonds and additional hydrogen.

10. A compound of the formula:

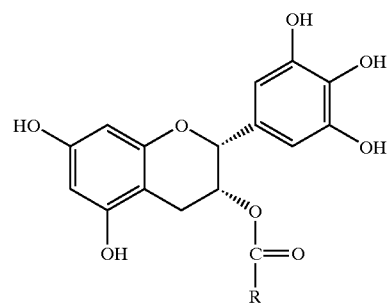

where R is

H

OH

CH$_3$

CH$_3$(CH$_2$)$_4$

CH$_3$(CH$_2$)$_8$

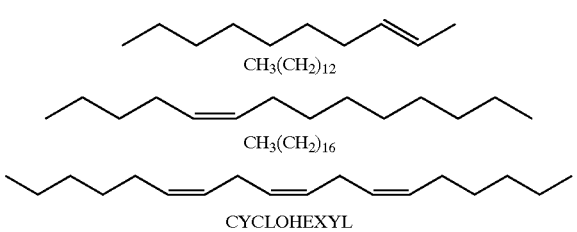

CH$_3$(CH$_2$)$_{12}$

CH$_3$(CH$_2$)$_{16}$

CYCLOHEXYL

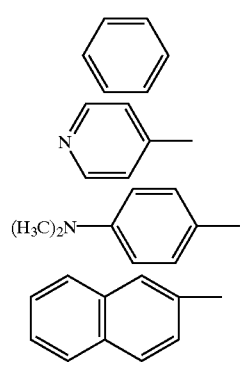

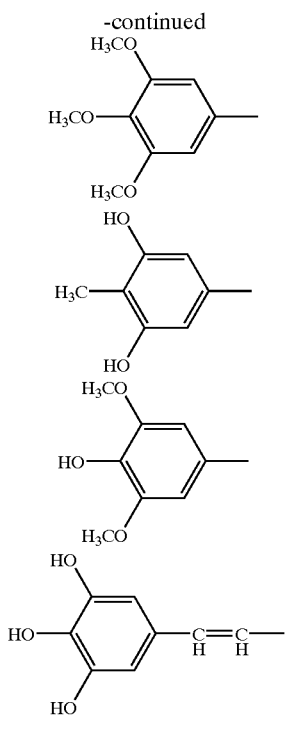

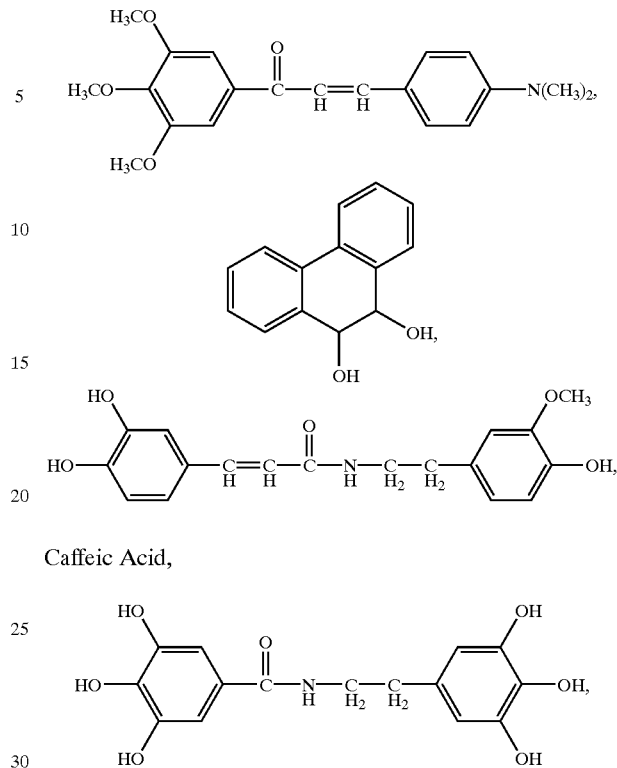

Caffeic Acid,

11. A method for the stabilization of compounds selected from the group consisting of the following:

Epicatechin Gallate,
Epigallocatechin Gallate,
Myricetin,
Quercitin,
Baicalein,
Fisetin,
Kaempferol,
Flavone,
Genistein,
Epigallocatechin,
Epicatechin,
Morin,
Alpha-napthoflavone,
Taxifolin,
Rutin,
Daidzein,
Beta-napthoflavone,
Chrysin,
Anthrarobin,
Bromopyrogallol Red,
Gossypol,
Pyrogallol Red,
Nordihydrogaiaretic Acid,
Caffeic Acid Phenethyl Ester,
Octyl Gallate,
Purpurogallin,
Hydroxydopamine,
Dodecylgallate,
Pyrocatechol Violet,
Pyrogallol,
Hematoxylin,
Exculetin,
Ellagic Acid,
Catechol,
Methylgallate,
Fraxetin,
Propylgallate,
Curcumin,
Tetrahydrocurcumin,
Demethoxy-tetrahydrocurcumin,
4-hydroxy-3-methoxy-cinnamaldehyde,
Coniferol,
4-(4-hydroxy-3-methoxyphenol)-3-buten-2-one,
Ferulic Acid,
Capsaicin,
Eugenol,
Purpurin,
Alizarin,
Menadione,
Coenzyme q,
2,5-dichloroindophenol,
Anthrarufin,
Lapachol,
Anthraflavic Acid,
Quinizarin,
T-butylhydroxyquinone,
Anthraquinone,
Gamma-Linolenic Acid C18:3 CIS 6.9,12,
Crocetin,
Alpha-Linolenic Acid C18:3 CIS 9,12,15,
Linoleic Acid C18:2 CIS 9,12,
Oleic Acid C18:1 CIS 9,
Conjugated Octadecadienoic Acid,
5,8,11,14-Ecostetraynoic Acid,
Stearic Acid C18:0,
Nordihydroguaiaretic Acid, Biochanin A,
Alizarin Red S,
Isopropyl Gallate,
Gallic Acid,
Alpha-Linolenic Acid Methyl Ester,
Gamma-Linolenic Acid Cholesterol Ester,
Gamma-Linolenic Acid Methyl Ester, where R is

H,
OH,
$CH_3$,
$CH_3(CH_2)_4$,
$CH_3(CH_2)_8$, $CH_3(CH_2)_{12}$, $CH_3(CH_2)_{16}$, comprising adding an effective amount of an inorganic acid, an organic acid, or a natural product that contains these acids to maintain the acidity of the therapeutic preparations of these compounds at pH 3.0 to pH 6.8.

12. A process of inhibiting 5α-reductase activity comprising the step of exposing 5α-reductase to an effective inhibiting amount of a compound selected from the group consisting of epicatechin, epicatechin-3-gallate, epigallocatechin, epigallocatechin-3-gallate and epigallocatechin derivatives represented by the structure:

where R is $CH_3(CH_2)_4$, $CH_3(CH_2)_6$, $C_9H_{17}$, $CH_3(CH_2)_{12}$, $C_{27}H_{29}$, a cyclohexyl group, a benzene group, -continued

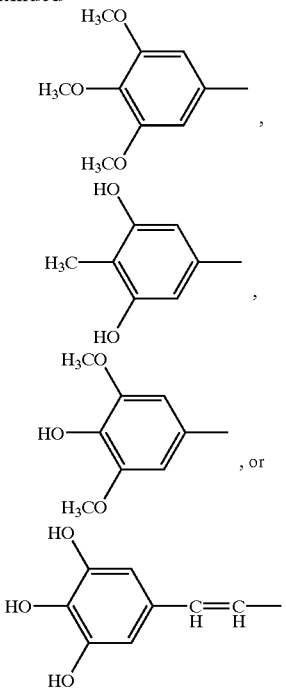
,

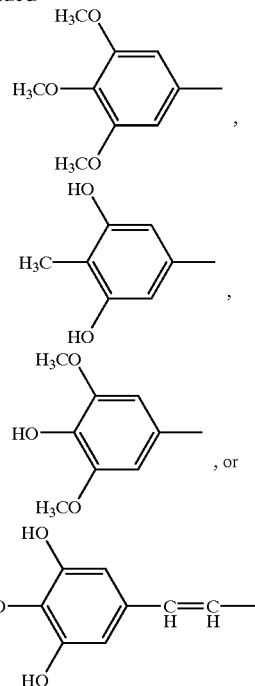
,

13. A process of treating prostate cancer in a subject in need of such treatment comprising the step of administering to the subject an effective therapeutic amount of a compound selected from the group consisting of epicatechin, epicatechin-3-gallate, epigallocatechin, epigallocatechin-3-gallate and epigallocatechin derivatives represented by the structure:

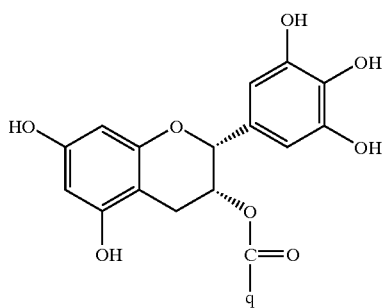

where R is $CH_3(CH_2)_4$, $CH_3(CH_2)_6$, $C_9H_{17}$, $CH_3(CH_2)_{12}$, $C_{27}H_{29}$, a cyclohexyl group, a benzene group,

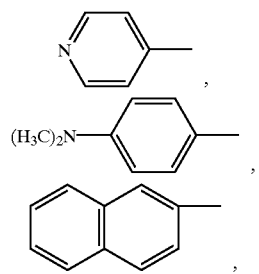

14. A process of treating breast cancer in a subject in need of such treatment comprising the step of administering to the subject an effective therapeutic amount of a compound selected from the group consisting of epicatechin, epicatechin-3-gallate, epigallocatechin, epigallocatechin-3-gallate and epigallocatechin derivatives represented by the structure:

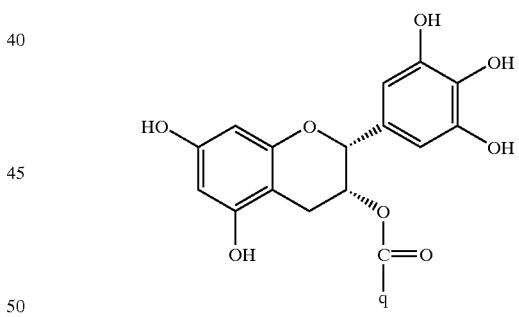

where R is $CH_3(CH_2)_4$, $CH_3(CH_2)_6$, $C_9H_{17}$, $CH_3(CH_2)_{12}$, $C_{27}H_{29}$, a cyclohexyl group, a benzene group,

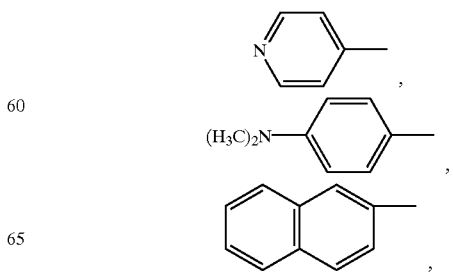

-continued

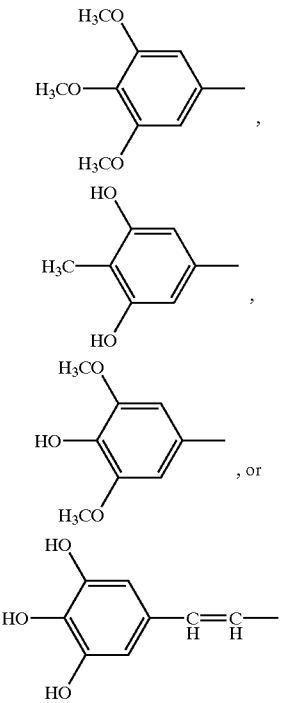, or

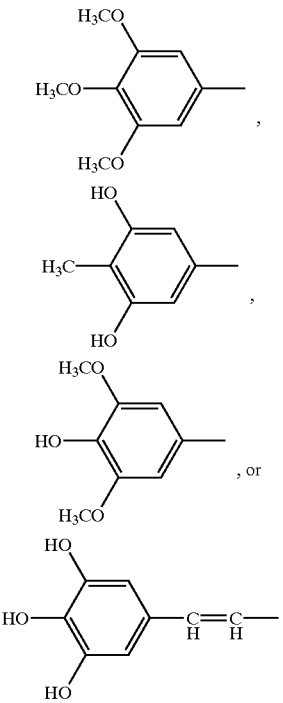, or

15. A process of treating baldness in a subject in need of such treatment comprising the step of administering to the subject an effective therapeutic amount of a compound selected from the group consisting epicatechin, epicatechin-3-gallate, epigallocatechin, epigallocatechin-3-gallate and epigallocatechin derivatives represented by the structure:

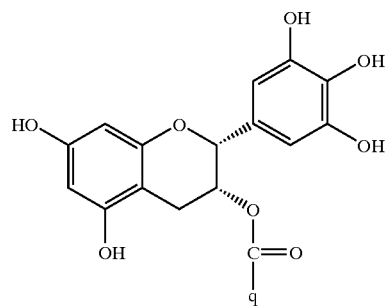

where R is $CH_3(CH_2)_4$, $CH_3(CH_2)_6$, $C_9H_{17}$, $CH_3(CH_2)_{12}$, $C_{27}H_{29}$, a cyclohexyl group, a benzene group,

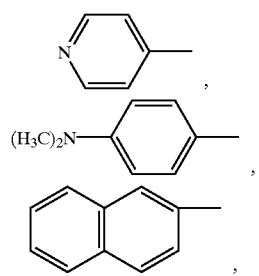

16. A process of treating a skin disorder in a subject in need of such treatment comprising the step of administering to the subject an effective therapeutic amount of a compound selected from the group consisting epicatechin, epicatechin-3-gallate, epigallocatechin, epigallocatechin-3-gallate and epigallocatechin derivatives represented by the structure:

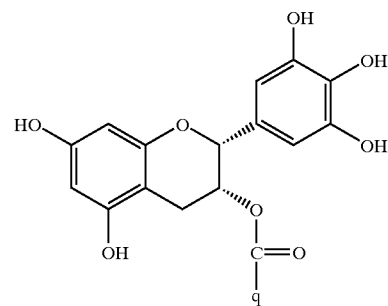

where R is $CH_3(CH_2)_4$, $CH_3(CH_2)_6$, $C_9H_{17}$, $CH_3(CH_2)_{12}$, $C_{27}H_{29}$, a cyclohexyl group, a benzene group,

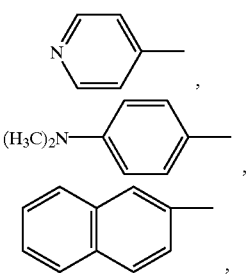

-continued

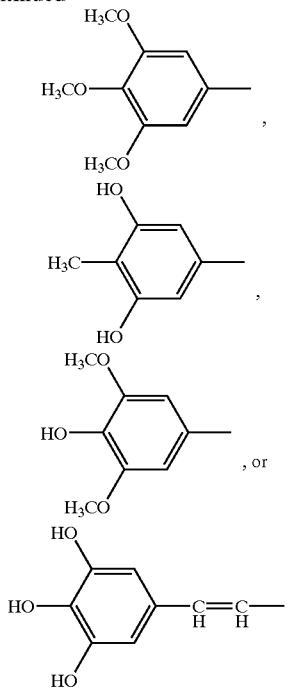,

17. A process of treating obesity in a subject in need of such treatment comprising the step of administering to the subject an effective therapeutic amount of a compound selected from the group consisting of epicatechin, epicatechin-3-gallate, epigallocatechin, epigallocatechin-3-gallate and epigallocatechin derivatives represented by the structure:

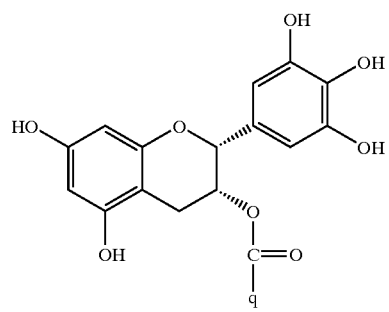

where R is $CH_3(CH_2)_4$, $CH_3(CH_2)_6$, $C_9H_{17}$, $CH_3(CH_2)_{12}$, $C_{27}H_{29}$, a cyclohexyl group, a benzene group,

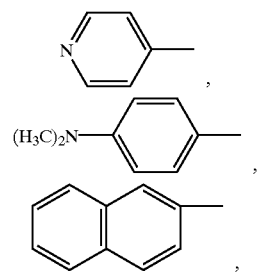,

-continued

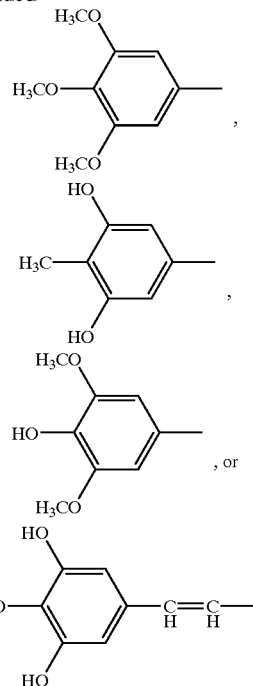,

18. A process of treating benign prostatic hyperplasia or prostatitis in a subject in need of such treatment comprising the step of administering to the subject an effective therapeutic amount of a compound selected from the group consisting of epicatechin, epicatechin-3-gallate, epigallocatechin, epigallocatechin-3-gallate and epigallocatechin derivatives represented by the structure:

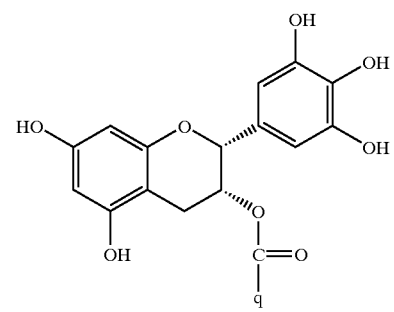

where R is $CH_3(CH_2)_4$, $CH_3(CH_2)_6$, $C_9H_{17}$, $CH_3(CH_2)_{12}$, $C_{27}H_{29}$, a cyclohexyl group, a benzene group,

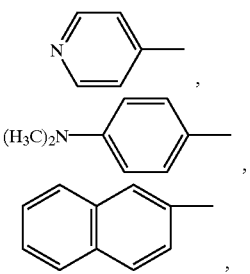,

-continued
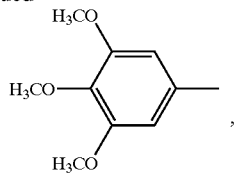,
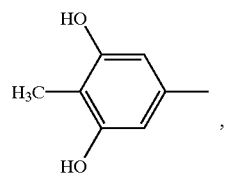,
-continued
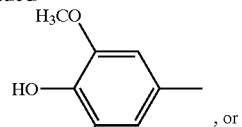, or
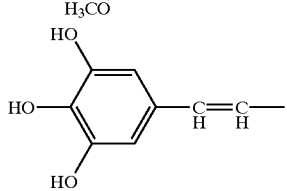.
* * * * *